United States Patent
Perlin et al.

(10) Patent No.: US 10,642,958 B1
(45) Date of Patent: May 5, 2020

(54) SUGGESTION ENGINE

(71) Applicant: C/HCA, Inc., Nashville, TN (US)

(72) Inventors: Jonathan Perlin, Nashville, TN (US); Paul Martin Paslick, Nashville, TN (US); Jim Najib Jirjis, Nashville, TN (US); William Michael Gregg, Nashville, TN (US); Thomas Andrew Doyle, Franklin, TN (US); Christian Krayer, Nolensville, TN (US); Karl Bradley Kehler, Nashville, TN (US); Sarah Buta, Arlington, MA (US); Erin Jospe, Newton, MA (US); Umesh Phirke, Newton, MA (US); Paul Brient, Wayland, MA (US)

(73) Assignee: C/HCA, Inc., Nashville, TN (US)

( * ) Notice: Subject to any disclaimer, the term of this patent is extended or adjusted under 35 U.S.C. 154(b) by 677 days.

(21) Appl. No.: 14/967,027

(22) Filed: Dec. 11, 2015

Related U.S. Application Data

(60) Provisional application No. 62/095,598, filed on Dec. 22, 2014, provisional application No. 62/163,220, filed on May 18, 2015.

(51) Int. Cl.
*G06Q 50/22* (2018.01)
*G06F 19/00* (2018.01)
(Continued)

(52) U.S. Cl.
CPC ...... *G06F 19/3418* (2013.01); *G06F 16/9535* (2019.01); *G16H 10/60* (2018.01); *H04L 67/306* (2013.01)

(58) Field of Classification Search
CPC .... G06Q 10/06; G06Q 10/0639; G06Q 50/24; G06F 19/325; G06F 19/00;
(Continued)

(56) References Cited

U.S. PATENT DOCUMENTS 6,629,937 B2   10/2003   Watrous
7,769,600 B2   8/2010    Iliff
(Continued)

OTHER PUBLICATIONS

U.S. Appl. No. 15/684,747, filed Aug. 23, 2017, Notice of Allowance dated Oct. 19, 2017, all pages.
(Continued)

*Primary Examiner* — Maroun P Kanaan
(74) *Attorney, Agent, or Firm* — Kilpatrick Townsend & Stockton LLP

(57) ABSTRACT

In some examples, a suggestion engine is provided to generate decision support output (DSO) based on data collected generation devices within a network. The DSO may be based on dependent users details, profile information for an authorized user associated with the dependent user, one or more knowledge artifacts, and/or other information related to a relationship between the dependent user and the authorized user. The DSO may include one or more suggestions, tasks, considerations, or the like. These may be presented in a customizable contextual user interface which presents DSO in a manner that considers the underlying context in which the dependent user exists. Based on a selection of a task or suggestion, a populator engine may populate one or more forms, which may be approved and provided to other authorized users. In addition, certain analytics data may be organized according to a performance indicator and included within a dashboard, which may be included in the contextual user interface.

21 Claims, 16 Drawing Sheets

(51) Int. Cl.
*H04L 29/08* (2006.01)
*G16H 10/60* (2018.01)
*G06F 16/9535* (2019.01)

(58) Field of Classification Search
CPC .. G06F 19/3456; G06F 19/3481; G06F 19/12; G06F 19/328; G06F 19/3475; G06F 19/3418; G06F 19/18; G06F 19/24; G06F 3/0484; G06F 9/542; G06F 3/04847; G16H 10/60; G16H 50/20; G16H 50/30; G16H 10/20; H04L 41/22; H04L 41/5032; H04L 41/5009; H04L 41/5012; H04L 41/5045
See application file for complete search history.

(56) References Cited

U.S. PATENT DOCUMENTS

| | | | |
|---|---|---|---|
| 8,094,009 B2 | 1/2012 | Allen et al. | |
| 9,060,683 B2 | 6/2015 | Tran | |
| 9,081,879 B2 | 7/2015 | Iliff | |
| 9,269,116 B2 | 2/2016 | Bulat | |
| 9,524,569 B2 | 12/2016 | Moore | |
| 9,779,611 B1 | 10/2017 | Krayer et al. | |
| 2001/0042119 A1 | 11/2001 | Urano | |
| 2004/0172222 A1 | 9/2004 | Simpson | |
| 2005/0075970 A1 | 4/2005 | Doyle | |
| 2005/0288965 A1 | 12/2005 | Eaton et al. | |
| 2006/0111941 A1 | 5/2006 | Blom | |
| 2006/0241978 A1 | 10/2006 | Yoshii | |
| 2007/0094046 A1 | 4/2007 | Cobbs | |
| 2007/0185390 A1 | 8/2007 | Perkins | |
| 2007/0250345 A1 | 10/2007 | Walker | |
| 2008/0091464 A1* | 4/2008 | Lipscher | G06Q 50/22 705/2 |
| 2008/0270189 A1 | 10/2008 | Howard | |
| 2009/0125334 A1 | 5/2009 | Krishnan et al. | |
| 2010/0094649 A1 | 4/2010 | White | |
| 2011/0046979 A1 | 2/2011 | Tulipano et al. | |
| 2012/0101847 A1* | 4/2012 | Johnson | G06Q 10/00 705/3 |
| 2012/0117476 A1 | 5/2012 | Siegrist | |
| 2012/0130734 A1 | 5/2012 | White | |
| 2012/0224057 A1 | 9/2012 | Gill et al. | |
| 2014/0067418 A1 | 3/2014 | Hyzy | |
| 2014/0188895 A1 | 7/2014 | Wang et al. | |
| 2014/0316813 A1 | 10/2014 | Bauer | |
| 2015/0154528 A1 | 6/2015 | Kharraz Tavakol | |
| 2015/0193583 A1* | 7/2015 | McNair | G16H 50/20 705/2 |
| 2016/0034986 A1 | 2/2016 | Ortiz | |
| 2016/0110502 A1 | 4/2016 | Bronson et al. | |
| 2016/0321430 A1 | 11/2016 | Eckman et al. | |
| 2017/0116373 A1* | 4/2017 | Ginsburg | G06F 19/322 |
| 2017/0293988 A1 | 10/2017 | Goyal | |

OTHER PUBLICATIONS

U.S. Appl. No. 15/357,745, filed Nov. 21, 2016, Notice of Allowance dated May 24, 2017, all pages.
Non-Final Office Action dated Mar. 18, 2019 in related U.S. Appl. No. 15/156,503, 39 pgs.
Non-Final Office Action dated Nov. 21, 2018 in related U.S. Appl. No. 15/902,897, 18 pgs.
Notice of Allowance dated Jan. 24, 2019 in related U.S. Appl. No. 15/902,897, 9 pgs.
Non-Final Office Action dated May 28, 2019, in U.S. Appl. No. 16/358,282, 16 pgs.
Final Office Action dated Sep. 12, 2019, in U.S. Appl. No. 15/156,503, 42 pgs.
Final Office Action dated Sep. 26, 2019, in U.S. Appl. No. 16/358,282, 17 pgs.

* cited by examiner

SUGGESTION ENGINE

RELATED APPLICATIONS

The present application claims the benefit of priority of U.S. Provisional Application No. 62/095,598, filed on Dec. 22, 2014, entitled, "Medical Suggestion Engine," and claims the benefit of priority of U.S. Provisional Application 62/163,220, filed on May 18, 2015, entitled "Risk Assessment and Event Detection" which are hereby incorporated by reference in their entirety.

BACKGROUND

This specification relates in general to suggestion generation systems and, but not by way of limitation, to generating suggestions for authorized users and providing suggestions to authorized users.

The amount of data generated each day continues to grow. In some industries, some of this data may be stored, while a majority of it may be processed and abandoned or ignored. Users working in these industries are beginning to rely more and on this data to make decisions. This may be especially true when the data is introduced as part of an operational flow. However, the time required to sort through stored data can create inefficiencies and the fact that other data may typically be ignored or abandoned may create liabilities.

BRIEF DESCRIPTION OF THE DRAWINGS

Various embodiments in accordance with the present disclosure will be described with reference to the drawings, in which.

DETAILED DESCRIPTION

Figure 1:
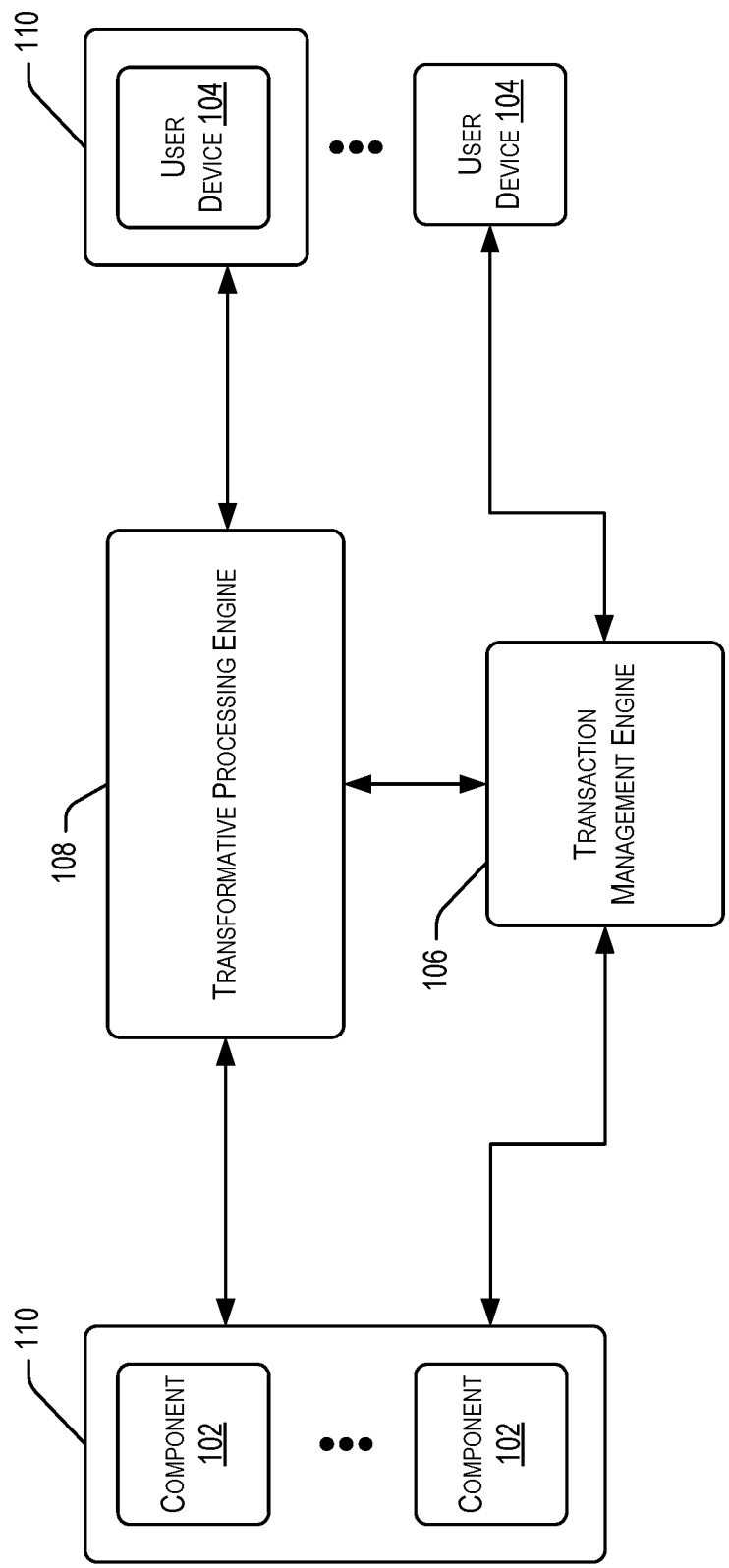
FIG. 1 is an example block diagram illustrating an environment in which techniques relating to generating contextual suggestions and providing contextual suggestions to authorized users as described herein may be implemented, according to at least one example.

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes may be made in the function and arrangement of elements without departing from the spirit and scope as set forth in the appended claims.

In one example, a suggestion engine is provided that generates suggestions within a provider network. The suggestion engine accesses information from many different sources in order to make informed suggestions that are particularized to a dependent user and an authorized user. For example, as an authorized user initiates an order corresponding to present conditions of the dependent user, the suggestion engine begins to determine a list of suggestions. To do so, the suggestion engine considers a profile of the authorized user and the dependent user's record (e.g., dependent user present conditions, demographic information, history, etc.). This information helps to provide context to what suggestions would be helpful for the authorized user. In addition, the suggestion engine considers a knowledge based organized into what are referred to herein as knowledge artifacts. The knowledge artifacts represent associations between certain situations (e.g., orders, diagnoses, etc.) and the outcomes in related cases. Some knowledge artifacts are determined programmatically or by human users from proprietary medical-related information within the provider network. Other knowledge artifacts are determined from medical-related information collected from sources external to the provider network. The suggestion engine considers the knowledge artifacts by comparing them to the care scenario to determine a list of suggestions. The suggestion engine also considers costs associated with the list of suggestions, availability of the suggestions, insurance payment constraints, and any other relevant factor that would be considered by an authorized user in determining a recommended course of treatment. These suggestions are then weighted by the outcomes associated with each suggestion. In this manner, the list of suggestions represents a list of likely orders, steps, acts, tests, procedures, or the like that the authorized user should consider while administering care to the dependent user.

In one example, a form populator engine is provided that populates forms within a provider network. The form populator engine determines which forms to populate based on an authorized user's selection of a course of treatment for a dependent user. The course of treatment may have been suggested to the authorized user by a suggestion engine. Thus, once the authorized user identifies the course of treatment, the suggestion engine determines a list of tasks corresponding to the course of treatment. The list of tasks may be future tasks that involve submission of related forms as a precondition for performance of the tasks. For example, a prescription form must be signed by the authorized user before it can be used by a pharmacist to fill the prescription. Once the authorized user identifies a particular task, the form populator engine populates some of the fields of a form corresponding to the particular task with the authorized user's information and/or the dependent user's information. The form populator engine then transmits the populated form populator to the authorized user for authorization, review, etc. prior to transmitting the populated form to a different authorized user for performance of the task.

In one example, a contextual user interface is provided for displaying medical-related information, e.g., suggestions, considerations, cart information, etc. on a user interface of a user device associated with an authorized user. To begin, a dependent user is associated with the authorized user in a provider network. Because the dependent user and the authorized user are associated, the medical-related information presented on the user interface can be tailored to treatment of the dependent user by the authorized user. Next, the authorized user selects a course of treatment for treating the dependent user. Indication of this selection is provided to the provider network such that the medical-related information can also be tailored to the course of treatment. Based on the selected course of treatment, a list of tasks (i.e., a form of medical-related information) related to the course of treatment are determined and provided for presentation. This determination depends not only on the course of treatment, but also on the profile information of the authorized user. The list of tasks are tasks that the authorized user should consider while administering care to the dependent user. Thus, the list of tasks may indicate other tests to administer, referrals to make, lab information to collect, and the like. The tasks are presented on the user interface in a manner that emphasizes certain more important tasks (e.g., based on the criticality of the task at the relevant point in the course of treatment), while at the same time deemphasizing relevant but less important tasks. Thus, the presentation and the determination of tasks are performed while considering the context in which the tasks are being determined and presented. Other medical-related information such as chart information for the dependent user is presented along with the tasks.

In one example, a dashboard is provided in which analytics data is presented. The dashboard is provided on a user interface of a user device. The dashboard includes updateable graphical representations of performance indicators (e.g., outcomes, visits, surgeries, etc.). In some examples, updateable graphical representations are presented as graphs, tables, or the like (e.g., in the form of application widgets) and organized based on the specialty and/or preferences of the authorized user. For example, for a particular performance indicator (e.g., outcomes), the analytics data relating to this indicator can be organized in a pie chart and presented in a way that informs a viewer (e.g., the authorized user) of his or her own performance. The analytics data may also be presented in a way that compares authorized users according to the performance indicators. The dashboard can be updated regularly. In some examples, the updates take place according to an update schedule, periodically, after the analytics data changes, or in any other suitable fashion.

Referring first to FIG. 1, a block diagram of an embodiment of an interaction system 100 is illustrated. Generally, in interaction system 100, data can be generated at one or more system components 102 and/or user devices 104. Transaction management engine 106 van manage the flow of communications within interaction system. Transformative processing engine 108 can receive, intercept, track, integrate, process and/or store such data.

Data flowing in interaction system 100 can include a set of communications. Each of one, some of all communications can include (for example) an encoding type, authentication credential, indication of a content size, identifier of a source device, identifier of a destination device, identifier pertaining to content in the communication (e.g., an identifier of an entity), a processing or reporting instruction, a procedure specification, transmission time stamp, and/or sensor measurement. Data may, or may not, selectively pertain to a particular entity and/or client. Data can, depending on the implementation, include individually identifiable information and/or de-identified information as it pertains to an entity and/or client. Data may, but need not, include protected information.

For example, a system component 102 can include, for example, a sensor to detect a sensor measurement and can thereafter generate and transmit a communication that reflects the sensor measurement. The communication may be transmitted at routine times and/or upon detecting a threshold (e.g., one or more) number of measurements or a measurement satisfying a transmission condition (e.g., exceeding a threshold value). In some instances, the sensor measurement corresponds to one reflecting a property of an object or entity (e.g., person) near the sensor. The communication may then include an identifier of the object or entity. The identifier can be determined, for example, based on detection of a nearby electronic tag (e.g., RFID tag), a detected user input received at a user interface of component 102 and/or data in a corresponding communication received from a user device.

As another example, a user device 104 can be configured to detect user input received at a user interface of the device. The user input can include, for example, an identifier of an object or entity, an instruction, a characterization of an object or entity, an identification of an assessment to be performed, a specification of an aggregation or data processing to be performed, and/or an identification of a destination for a data-analysis report. User device 104 can further be configured to detect user input requesting particular data, to generate a request communication (e.g., to be sent to transformative processing engine), to receive the requested data and/or to present the received data.

Data can include information that identifies a person, such as personal information and/or demographic information. For example, the information can identify a person's name, age, sex, race, physical address, phone number, email address and/or social security number. Data may include information collected by a government agent, employer, insurer, or school or university, that relates to a past, present, or future condition or status (e.g., pertaining to employment, political involvement, occupation, health, or financial status) of any individual. For example, data may include information about past events.

Data may identify an entity being evaluated and/or one at least partly performing an evaluation. For example, a communication may identify a first company as one being evaluated and a second company as one evaluating a quality of a product of the first company. As another example, a communication may identify a first service plan of a first company as one providing an Internet network and may identify one or more users providing speed checks over the network.

The depicted engines, devices and/or components can communicate over one or more networks. A network of one or more networks can include a wired network (e.g., fiber, ethernet, powerline ethernet, ethernet over coaxial cable, digital signal line (DSL), or the like), wireless network (e.g., Zigbee™, Bluetooth™, WiFi™, IR, UWB, WiFi-Direct, BLE, cellular, Long-Term Evolution (LTE), WiMax™, or the like), local area network, the Internet and/or a combination thereof. It will be appreciated that, while one or more components 102 and one or more user devices 104 are illustrated as communicating via transformative processing engine 108 and/or transaction management engine 106, this specification is not so limited. For example, each of one or more components 102 may communicate with each of one or more user devices 104 directly via other or the same communication networks.

A component 102 can be configured to detect, process and/or receive data, such as environmental data, geophysical data, biometric data, chemical data (e.g., chemical composition or concentration analysis data), and/or network data. The data can be based on data detected, for example, via a sensor, received signal or user input. A user device 104 can include a device configured to receive data from a user and/or present data to a user. It will be appreciated that, in some instances, a component 102 is also a user device 104 and vice-versa. For example, a single device can be configured to detect sensor measurements, receive user input and present output.

A component 102 can be configured to generate a communication that is in one or more formats, some of which can be proprietary. For example, an imaging machine (e.g., one of one or more components 102) manufactured by company A, located within a first facility (e.g., facility 110), and belonging to a first client, may save and transfer data in a first format. An imaging machine (e.g., one of one or more components 102) manufactured by company B, located within the first facility (e.g., facility 110), and belonging to the first client, may save and transfer data in a second format. In some examples, data from certain components is transformed, translated, or otherwise adjusted to be recognizable by transformative processing engine 108. Thus, continuing with the example from above, when the imaging machines manufactured by companies A and B are located within the first facility belonging to the first client, they may nevertheless save and transfer data in different formats. In some examples, one or more components 102 communicate using a defined format.

In some examples, each of one or more components 102 are each associated with one or more clients within a same or different interaction systems. For example, certain ones of one or more components 102 may be associated with a first client, while other ones of one or more components 102 may be associated with a second client. Additionally, each of one or more components 102 may be associated with a facility 110 (e.g., client facility). Each facility 110 may correspond to a single location and/or processing focus. Exemplary types of facilities include server farm facilities, web-server facilities, data-storage facilities, technical-support facilities, telecommunication facilities, care facilities and/or business operation facilities. For example, a first facility may include a structure at a first location at which one or more resources (e.g., computational resources, equipment resources, laboratory resources and/or human resources) are provided. Each of the one or more resources may be of a first type in a first set of types. A resource type can be identified based on, for example, a characteristic of the resource (e.g., sensor inclusion) and/or a capability of providing each of one or more services. Thus, for example, resources at a first facility may be better configured for handling a particular type of service requests compared to those in another facility. As another examples, different facilities may include resources of similar or same types but may vary in terms of, for example, user accessibility, location, managing client, etc.

Transmission of data from one or more components 102 to transformative processing engine 108 may be triggered by a variety of different events. For example, the data may be transmitted periodically, upon detection of an event (e.g., completion of an analysis or end of a procedure), upon detection of an event defined by a rule (e.g., a user-defined rule), upon receiving user input triggering the transmission, or upon receiving a data request from transformative processing engine 108. Each transmission can include, e.g., a single record pertaining to a single entity, object, procedure, or analysis or multiple records pertaining to multiple entities, objects, procedures, or analyses.

In some examples, at least some of one or more user devices 104 are associated with facility 110. In some examples, at least some of one or more user devices 104 need not be associated with facility 110 or any other facility. Similar to one or more components 102, one or more user devices 104 may be capable of receiving, generating, processing and/or transmitting data. Examples of one or more user devices 104 include, for example, a computer, a mobile device, a smart phone, a laptop, an electronic badge, a set-top box, a thin client device, a tablet, a pager, and other similar user devices). One or more user devices 104 may be configured to run one or more applications developed for interacting with data collected by transformative processing engine 108. For example, those user devices of one or more user devices 104 that are not associated with facility 110 may be configured to run one or more third-party applications that may rely in part on the data gathered by transformative processing engine 108.

Each of one or more components 102 and one or more user devices 104 may be utilized by one or more users (not shown). Each of the one or more users may be associated with one or more clients. For example, one of the one or more users can be associated with a client as a result of being employed by the client, physically located at a location of the client, being an agent of the client or receiving a service from the client.

In some examples, one or more components 102 and one or more user devices 104 may communicate with transformative processing engine 108 and transaction management engine 106 via different information formats, different proprietary protocols, different encryption techniques, different languages, different machine languages, and the like. As will be discussed with reference to FIG. 2, transformative processing engine 108 is configured to receive these many different communications from one or more components 102, and in some examples from one or more user devices 104, in their native formats and transform them into any of one or more formats. The received and/or transformed communications can be transmitted to one or more other devices (e.g., transaction management engine 106, an entity device and/or a user device) and/or locally or remotely stored. In some examples, transformative processing engine 108 receives data in a particular format (e.g., the HL7 format) or conforming to any other suitable format and/or is configured to transform received data to conform with the particular format.

One or more components 102 of facility 110 can include and/or has access to a local or remote memory for storing generated data. In some examples, the data is stored by one or more servers local to facility 110. Such storage may enable facility 110 to retain locally data pertaining to its facility prior to (or in conjunction with) the data being shared with transformative processing engine 108 and/or transaction management engine 106. In some examples, the one or more servers of facility 110 share data directly with a record service (not shown), and the record service makes the data available to transformative processing engine 108 and/or transaction management engine 106. Once an electronic record is updated at facility 110, an indication of the update may be provide to the record service. The record service may then update a corresponding record associated with the electronic record.

The record service can be granted access to the data generated and/or transmitted by one or more components 102. In some examples, the record service includes a server or a plurality of servers arranged in a cluster or the like. These server(s) of the record service can process and/or store data generated by one or more components 102. For example, one or more records can be generated for each entity (e.g., each record corresponding to a different entity or being shared across entities). Upon receiving a communication with data from an component (or facility), the record service can identify a corresponding record and update the record to include the data (or processed version thereof). In some examples, the record service provides data to transformative processing engine 108.

Facility 110 can include one at which a resource is located and/or service is provided. Irrespective of the type of facility, facility 110 may update data, maintain data, and communicate data to transformative processing engine 108. At least some of the data may be stored local to facility 110.

A user interacting with a user device 104 can include, for example, a client customer, client agent and/or a third party. A user may interact with user device 104 and/or component 102 so as to, for example, facilitate or initiate data collection (e.g., by a component 102), provide data, initiate transmission of a data request, access data and/or initiate transmission of a data-processing or data-storage instruction. In some instances, one or more user devices 104 may operate according to a private and/or proprietary network or protocols. In other examples, one or more user devices 104 may operate on public networks. In any case, however, transformative processing engine 108 can have access to the one or more components and can communicate with them via a public, private and/or proprietary network or protocols. The use of one or more private and/or proprietary protocols can promote secure transfer of data.

Figure 2:
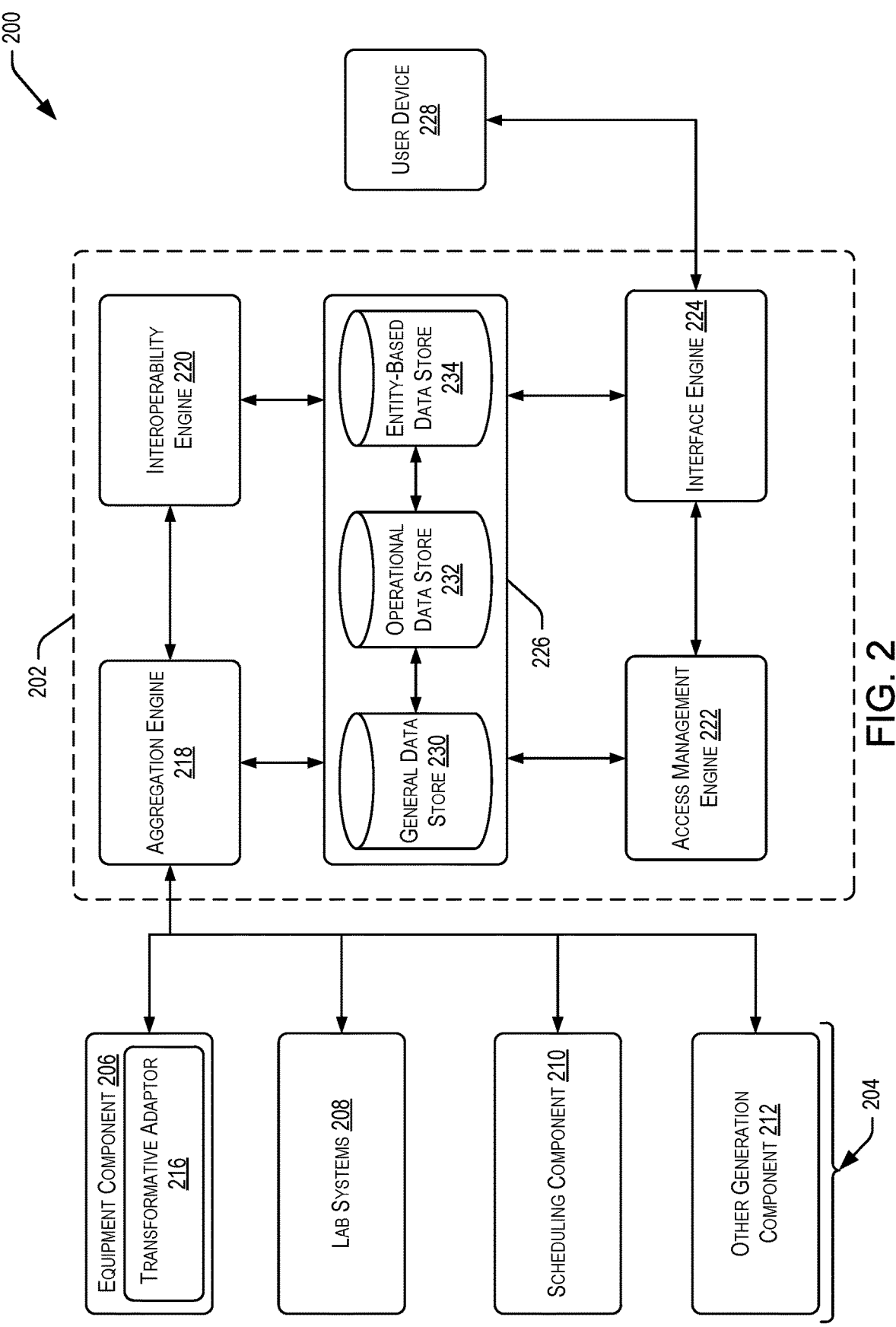
FIG. 2 is an example block diagram illustrating an environment in which techniques relating to generating contextual suggestions and providing contextual suggestions to authorized users as described herein may be implemented, according to at least one example.

Referring next to FIG. 2, a block diagram of an example of an interaction system 200 is shown. Interaction system 200 includes a transformative processing engine 202. Transformative processing engine 202 is an example of transformative processing engine 108 discussed with reference to FIG. 1. Interaction system 200 also includes one or more generation components 204. In particular, one or more generation components 204 includes an equipment component 206, a lab systems component 208, a scheduling component 210 and other generation component 212. One or more generation components 204 are examples of one or more components 102 discussed with reference to FIG. 1.

Generally, one or more generation components 204 includes any suitable device or system capable of generating data in the context of an interaction system. For example, the other generation component 212 may include a sensor on a door, and equipment component 206 may include a sophisticated computer-controlled laser device. In either case, each generation component generates some type of data. For example, the data provided by the sensor may be used to address security concerns or assessing heating, ventilating, and air conditioning (HVAC) costs for an institution. The data provided by the laser device may have been provided while engaged in a procedure and may then be used by other entities in the future to decide how to use the device.

As discussed in further detail herein, data generated by one or more generation components 204 can be of a variety of formats, some of which may be proprietary. For example, a single component can generate data in multiple formats, different components can generate data in different formats, and/or different component types can result in generation of data in different formats. In some instances, formatting of a data can depend on a service having been provided, a user initiating data generation, a destination to receive the data, a location at which a service was provided, etc. In some examples, a typical interaction system includes thousands of generation components producing data in hundreds of formats. In order to harness the power that comes from such a large amount of data to make informed decisions, it is desirable that all, or at least a large portion of the data, is shared. Use of transformative processing engine 202 in accordance with techniques described herein may achieve this design—making large amounts of data, in many different originating formats available to various types of users, via one or more interfaces.

While one or more generation components 204 are illustrated adjacent to each other, it is understood that each may be located within one facility or that the components may be spread out among many facilities. In addition, in some examples, one or more generation components 204 belong to different clients.

Turning now to equipment component 206, this component includes any machine, contrivance, implant, or other similar related article, that is intended to aid in reaching a particular objective. In some instances, equipment component 206 includes one or more sensors to detect environmental or other stimuli. Equipment component 206 can include, for example, equipment to monitor a stimulus, detect stimulus changes, detect stimulus-indicative values, and so on. Exemplary equipment components 206 include an imaging device, a device that detects and characterizes electrical signals, a device that detects pressure, and/or a device that detects concentration of one or more particular elements, compounds and/or gases.

As illustrated, equipment component 206 includes transformative adaptor 216. In some examples, transformative adaptor 216 is a device that transforms, translates, converts, or otherwise adjusts output data from equipment component 206. For example, an equipment component 206 can be a scanner that outputs its results in format A, but the majority of other scanners in the interaction system output their results in format B. Transformative adaptor 216 may be implemented to convert or otherwise adjust the results in format A to conform closer to format B. For example, the conversion from format A to format B may be performed using a conversion rule, which may be user-define or learned. Transformative processing engine 202 may perform similar tasks as it relates to all data generated within interaction system 200. In this manner, transformative adaptor 216 can perform an initial step in the process of transformation, translation, conversion, or adjustment of the output of equipment component 206. In some examples, transformative adaptor 216 is implemented in hardware, software, or any suitable combination of both. In some examples, other transformative adaptors (not shown) may be implemented within others of one or more generation components 204. In some examples, equipment component 206 may not include transformative adaptor 216.

Lab systems component 208 includes any suitable laboratory equipment or system that is intended to analyze material, such as biological material. This includes, for example, laboratory equipment that analyzes biological samples; electric microscopes; ultracentrifuges; data collection devices, including Kymographs, sensors connected to a computer to collect data; monitoring devices; computers used to report results of lab tests, and other similar laboratory equipment. Each of the above-listed components generates data that is provided (directly or indirectly) to transformative processing engine 202.

Scheduling component 210 includes any suitable computing devices used for business-related purposes with respect to interaction system 200. For example, scheduling component 210 can be configured to schedule a resource for allocation for a particular entity during a particular time slot. Scheduling component 210 can monitor a schedule for the resource and can identify one or more available time slots that may be secured by a particular entity. Upon receiving a scheduling indication, scheduling component 210 may update a schedule of a resource to reflect that a particular time slot is to be allocated for service of a particular entity.

Each of one or more generation components 204 and the user device 228 may include individual and/or shared storage systems, one or more processors, a user interface, a network connectivity device, and one or more ports. The storage system include memory that may be implemented, e.g., using magnetic storage media, flash memory, other semiconductor memory (e.g., DRAM, SRAM), or any other non-transitory storage medium, or a combination of media, and can include volatile and/or non-volatile media. The storage systems may also be configured to store computer-executable code or instructions for interacting with the user interface and/or for one or more applications programs, such as an application program for collecting data generated by the particular generation component.

The one or more processors may be configured to access the operating system and application programs stored within the storage systems, and may also be configured to execute such program code. The one or more processors can be implemented as one or more integrated circuits, e.g., one or more single-core or multi-core microprocessors or microcontrollers, examples of which are known in the art. In operation, the one or more processors can control the operation of the particular component. The one or more processors may access and execute the program code and at any given time.

The user interface can include any combination of input and output devices. In some instances, a user can operate input devices of the user interface to invoke the functionality of the particular component or user device. For example, the user interface may enable the user to view, hear, and/or otherwise experience output from component or user device via the output devices of the user interface. Examples of output devices include a display, speakers, and the like.

The network connectivity device may enable the component or user device to communicate with transformative processing engine 202 and other components or other user devices via one or more networks. The one or more networks may include any suitable combination of cable, cellular, radio, digital subscriber line, or any other suitable network, which may be wired and/or wireless. In some examples, the network connectivity device may enable the component or the user device to communicate wirelessly with various other components and/or transformative processing engine 202. For example, the components may include circuitry to enable data communication over a wireless medium, e.g., using near-field communication (NFC), Bluetooth Low Energy, Bluetooth® (a family of standards promulgated by Bluetooth SIG, Inc.), Zigbee, Wi-Fi (IEEE 802.11 family standards), or other protocols for wireless data communication.

The one or more ports may enable the component or the user device to receive data from one or more sensors. The sensors may be any suitable type of sensor to capture data. Such captured data may be shared with transformative processing engine 202 in accordance with techniques described herein. In some examples, the sensors may also be configured to detect the component's or the user device's location and other details about the component or the user device. In some examples, the component and user device may include global positioning chips for determining a geolocation. Such geolocation information may be relevant to analyzing the data provided by the component or the user device located at the geographic location.

Transformative processing engine 202 includes an aggregation engine 218, an interoperability engine 220, an access management engine 222, an interface engine 224, and a data store 226. Generally aggregation engine 218 is configured to collect data from multiple communications. The data may be from one or multiple generation components 204 and/or may be of a same or different formats. Aggregation engine 218 may be configured to perform one or more operations on the collected data. For example, aggregation engine 218 may tag data, log data, perform protocol conversion, and may support one-to-many communications. The collection may be asynchronous. In some examples, the data has been saved locally in connection with one or more generation components 204 in many different formats having many different data structures.

Aggregation engine 218 can identify data to be aggregated based on, for example, intra-communication data, a current time, a source generation component, and/or one or more aggregation rules. For example, an aggregation rule may specify that data is to be aggregated across all communications that include content with a same entity identifier. An aggregation may be dynamic. For example, aggregated data may reflect that from within a most recent 12-hour period. Thus, an aggregation may be updated in time to exclude older data from the aggregation and to include newer data.

Aggregation engine 218 can be configured to provide data from one or more communications to interoperability engine 220. Interoperability engine 220 can be configured to perform one or more operations on the received data and store it in data store 226. For example, interoperability engine 220 may perform semantic tagging and indexing of data. This may include extracting field values from data, categorizing data (e.g., by type of data, characteristic of an entity, location of facility, characteristic of facility, and the like), anonymizing or partially-anonymizing data, and the like. Interoperability engine 220 may also include a high availability cache, an alerts engine and a rules engine. In some examples, interoperability engine 220 operates synchronously.

From interoperability engine 220, data flows to data store 226. Data store 226 (and any other data store discussed herein) may include one or more data stores, which may be distributed throughout two or more different locations (e.g., present on different devices, which can include devices of different entities and/or a cloud server). In some examples, data store 226 includes a general data store 230, an operational data store 232, and an entity-based data store 234. Within each of the data stores 230, 232, and 234 is stored data. Depending on the structure of the particular data store, certain data stores may include rules for reading and writing. The data stores 230, 232, and 234 may include records, tables, arrays, and the like, which may be relational or non-relational. Depending on the data store, records for individual entities, business and analytics information, output data from one or more generation components 204, and the like may be retained. The data within the data stores 230, 232, and 234 include elements or tags such that a particular data (e.g., for a single entity, protocol, etc.) can be retrieved.

Access management engine 222 is configured to manage access to features of transformative processing engine 202, including access to the data retained in data store 226. For example, access management engine 222 may verify that a user device such as user device 228 is authorized to access data store 226. To verify the user device 228, access management engine 222 may require that a user of the user device 228 input a username and password, have a profile associated with the interaction system, have paid a subscription fee associated with access to data store 226, and the like. Access management engine 222 may also verify that the user device 228 has an IP address or geographical location that corresponds to an authorized list, that the user device 228 includes a plug-in for properly accessing data store 226, that the user device 228 is running certain applications required to access data store 226, and the like.

Interface engine 224 is configured to retrieve the data from data store 226 and provide one or more interfaces for interacting with elements of transformative processing engine 202. For example, interface engine 224 includes an interface by which an application running on user device 228 can access portions of data within data store 226.

Figure 3:
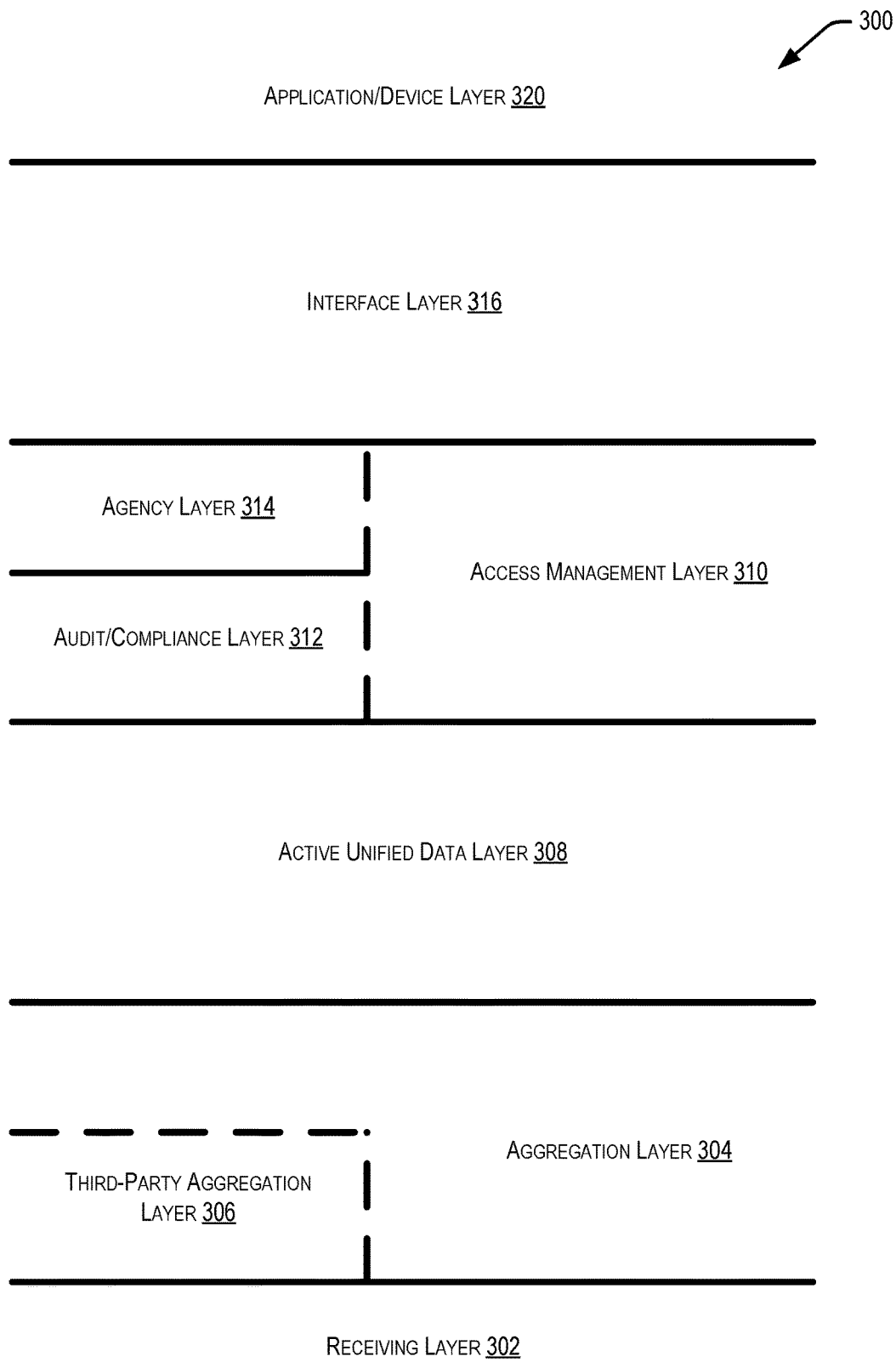
FIG. 3 is an example schematic model illustrating an a network communication model in which techniques relating to generating contextual suggestions and providing contextual suggestions to authorized users as described herein may be implemented, according to at least one example.

Turning next to FIG. 3, an architecture stack 300 is shown. In some examples, techniques relating management of data are implemented in accordance with architecture stack 300. And while architecture stack 300 is illustrated as having a particular structure, it is understood that other structures, including those with more or less layers than illustrated, is within the scope of this specification. In some examples, architecture stack 300 is implemented across an interaction system having a plurality of systems belonging to the same client or spread across different clients. Thus, architecture stack 300 can be used to integrate different systems of different organizations, entities, and the like and to provide a fluid sharing of information among elements within the interaction system and without the interaction system. In some instances, a multi-layer part of architecture stack 300 is implemented at a single system or device within an interaction system.

The different layers of architecture stack 300 will be described generally with reference to FIG. 3 and in detail with reference to subsequent figures. Architecture stack 300 includes a receiving layer 302 as the bottom-most layer. Receiving layer 302 includes receiving data from elements that share data with other elements within an aggregation layer 304. For example, as detailed herein, receiving layer 302 can include receiving data from generation components that generate data. As such, receiving layer 302 is where data that has been created is received. In some examples, the data within receiving layer 302 may be in its raw formats. The output may then be transmitted to aggregation layer 304. In some examples, components of receiving layer 302 may have complimentary layers to facilitate data transfer. For example, the components may include a data generation and/or a data transmission layer for providing data to receiving layer 302.

Elements of aggregation layer 304 aggregate the data generated by the elements of receiving layer 302. For example, the elements of aggregation layer 304 may include aggregation engines that collect data from generation components located within receiving layer 302. Such aggregation may be performed periodically, in response to a user request, according to a schedule, or in any other suitable manner. In some examples, data of aggregation layer 304 may be aggregated according to input and/or rules and may aggregate across records pertaining to, e.g., a facility, entity, time period, characteristic (e.g., demographic characteristic or condition), outcome, and any other suitable input and/or rules. The aggregation may include compiling the data, generating a distribution, generating a statistic pertaining to the data (e.g., average, median, extremum or variance), converting the data, transforming the data to different formats, and the like.

Next, architecture stack 300 includes an active unified data layer 308. Elements of active unified data layer 308 receive data from the elements of the other layers and store such data in a unified manner. In some examples, this may include storing the data in a manner that allows for later searching and retrieval using a defined set of method calls, techniques, and or procedures. For example, the data may be stored such that a different application can access the data in a standard or unified manner. Thus, elements of active unified data layer 308 may receive information collected or generated within aggregation layer 304 and make certain adjustments to the data (e.g., translations, tagging, indexing, creation of rules for accessing the data, conversion of formatting of the data, generation of compressed versions, and the like) prior to retaining the data within one or more data stores accessible within active unified data layer 308.

Architecture stack 300 also includes an access management layer 310, which can include an audit/compliance layer 312 and/or an agency layer 314. Access management layer 310 includes elements to manage access to the data. For example, access management layer 310 may include elements to verify user login credentials, IP addresses associated with a user device, and the like prior to granting the user access to data stored within active unified data layer 308.

Audit/compliance layer 312 includes elements to audit other elements of architecture stack 300 and ensure compliance with operating procedures. For example, this may include tracking and monitoring the other elements of access management layer 310.

Agency layer 314 includes an access location (e.g., a virtual private network, a data feed, or the like) for elements of agencies that are interested in the operations of the interaction system in which architecture stack 300 is implemented. For example, agency layer 314 may allow a governmental entity access to some elements within architecture stack 300. This may be achieved by providing the governmental entity a direct conduit (perhaps by a virtual private network) to the elements of access management layer 310 and the data within active unified data layer 308. Audit/compliance layer 312 and agency layer 314 are sub-layers of access management layer 310.

Architecture stack 300 also includes interface layer 316. Interface layer 316 provides interfaces for users to interact with the other elements of architecture stack 300. For example, clients, entities, administrators, and others belonging to the interaction system may utilize one or more user devices (interacting within application/device layer 320) to access the data stored within active unified data layer 308. In some examples, the users may be unrelated to the interaction system (e.g., ordinary users, research universities, for profit and non-profit research organizations, organizations, and the like) and may use applications (not shown) to access the elements within architecture stack 300 via one or more interfaces (e.g., to access data stored within active unified data layer 308). Such applications may have been developed by the interaction system or by third-parties Finally, architecture stack 300 includes application/device layer 320. Application/device layer 320 includes user devices and applications for interacting with the other elements of architecture stack 300 via the elements of interface layer 316. For example, the applications may be web-based applications, entity portals, mobile applications, widgets, and the like for accessing the data. These applications may run on one or more user devices. The user devices may be any suitable user device as detailed herein.

Figure 4:
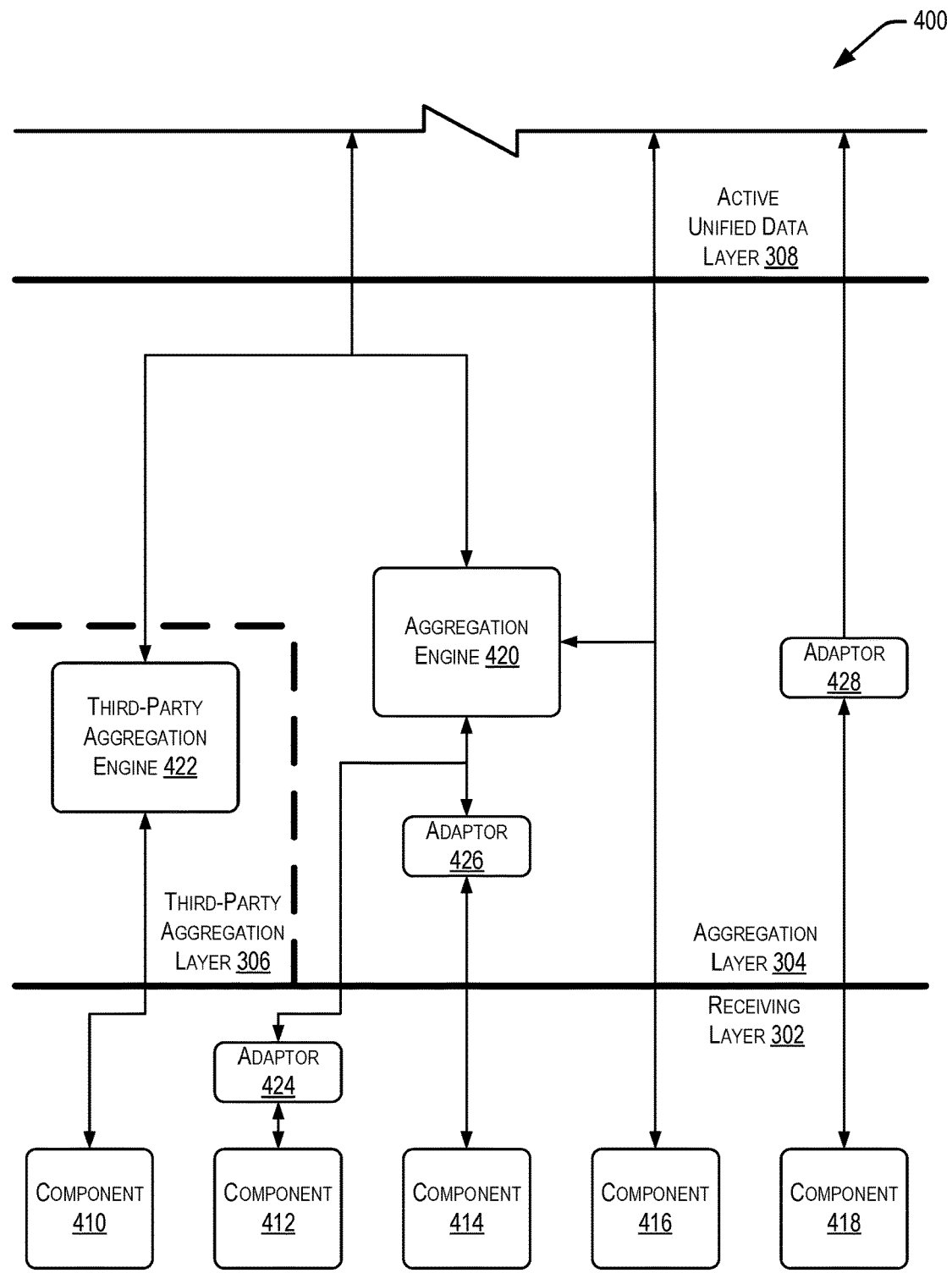
FIG. 4 is an example schematic model illustrating an aspect of the network communication model of FIG. 3 in more detail.

Turning next to FIG. 4, a diagram 400 is shown that depicts a portion of architecture stack 300 according to an embodiment of the invention. In particular, the diagram 400 includes receiving layer 302, aggregation layer 304, aggregation layer 306, and a portion of active unified data layer 308. Receiving layer 302 receives data from one or more components 410-418. Components 410-418 are examples of one or more generation components 204. Components 410-418 may be spread across multiple facilities within a single or multiple clients. In some examples, components 410-418 may include complimentary layers to facilitate data transmission. For example, components 410-418 may include a transmission layer, generation layer, and/or a receiving layer to communicate data at receiving layer 302 and, in some examples, receive data from receiving layer 302.

In some instances, two or more of components 410-418 generate data according to different formats. The data can then be transformed, translated, or otherwise adjusted before an aggregation engine 420 (e.g., aggregation engine 218) or a third-party aggregation engine 422 (e.g., aggregation engine 218) collects the data. In some examples, the adjustment takes place within receiving layer 302. Thus, an adaptor 424 is associated with component 412 located in receiving layer 302. Adaptor 424 is an example of transformative adaptor 216. Adaptor 424 is implemented, as appropriate, in hardware, software, or any suitable combination of both. For example, transformative adaptor 216 may be a bolt-on adaptor that adjusts data as such data leaves component 412.

Other adaptors, such as adaptor 426 and adaptor 428, are implemented within aggregation layer 304. These adaptors can function in a similar manner as adaptor 424. In some examples, the data provided by component 414 is transmitted through adaptor 426 prior to being directed to aggregation engine 420. The data provided by component 416 is transmitted through aggregation layer 304 and/or enters aggregation engine 420 without having first traveled through an adaptor. The data provided by component 418 is transmitted through aggregation layer 304 and through adaptor 428. In some examples, component 418 provides for streaming of data. The data provided by component 410 is transmitted directly to third-party aggregation engine 422.

Aggregation engine 420 and third-party aggregation engine 422 function in a similar manner. In some examples, third-party aggregation engine 422 is operated by a different entity than the entity that operates aggregation engine 420 and may belong to different clients or a different interaction system. This may be because the data collected by third-party aggregation engine 422 differs in some way from the data collected by aggregation engine 420. In any event, aggregation engine 420 is configured to perform integration of data, including generic integration. For example, aggregation engine 420 performs one or more operations on data including tagging, logging, and protocol conversion. Aggregation engine 420 also supports one-to-many communications of data. In some examples, data flows between aggregation engine 420, the third-party aggregation engine 422, and some of components 410-418 and elements of active unified data layer 308.

Figure 5:
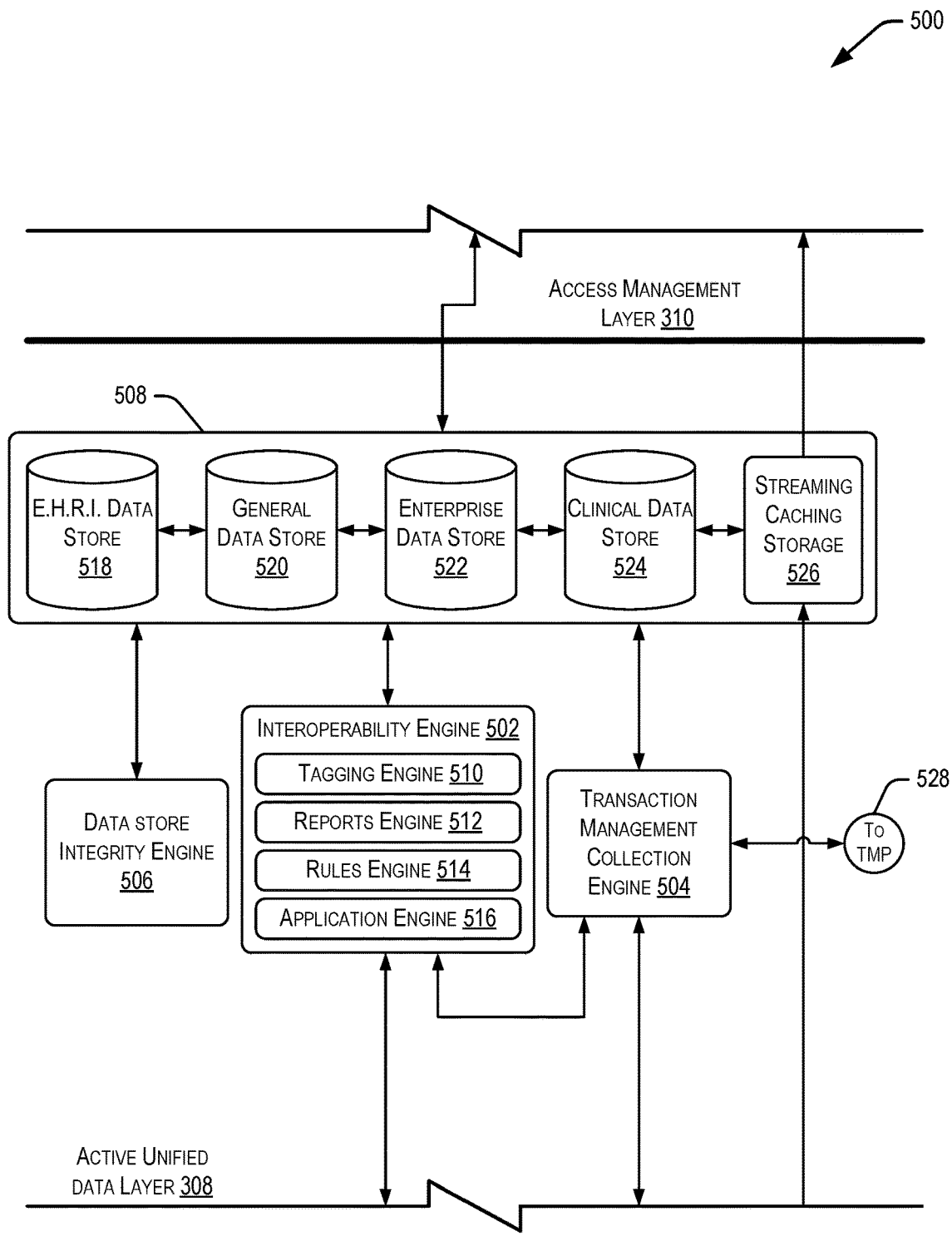
FIG. 5 is an example schematic model illustrating an aspect of the network communication model of FIG. 3 in more detail.

Referring next to FIG. 5, a diagram 500 is shown that depicts a portion of architecture stack 300 according to an embodiment of the invention. In particular, diagram 500 includes active unified data layer 308 and a portion of access management layer 310. Active unified data layer 308, as illustrated in diagram 500, includes an interoperability engine 502 (e.g., interoperability engine 220), a transaction management collection engine 504, a data store integrity engine 506, and a data store 508 (e.g., data store 226). Generally, interoperability engine 502 receives data from elements within aggregation layer 304 (e.g., from aggregation engine 420) and performs one or more operations with respect to the data. Interoperability engine 502 also facilitates storage of at least a portion of the processed information in data store 508.

Transaction management collection engine 504 is implemented as part of transaction management engine 106. Transaction management collection engine 504 is configured to generate message indicators identifying flows of data by and between elements of an interaction system implemented using the techniques described herein. The flows of information include messages which include data, and the message indicators include unique message identifiers that can be used to identify the messages. The unique message identifiers include information that can be used to uniquely identify the messages. For example, a unique message identifier for a particular message can include a concatenation of the following information stored in a table: a source application, a facility, a message type, and a message control identification (ID). The unique message identifier can also be the message control ID. The unique message identifier may be created as messages including data are transmitted from aggregation layer 304. The table may be stored in association with the transaction management platform 528.

In some examples, the table also includes information for tracking the progress of the message from an origination node to a destination node. For example, typically when a message (e.g., any communication of data) is first received by transformative processing engine 108 (e.g., interoperability engine 502), transaction management engine 106 (e.g., transaction management collection engine 504 of transaction management engine 106) may generate a unique identifier for the message in order to track that message as it moves throughout the interaction system. The unique identifier may be included in the header of the message such that when the next node (e.g., component, device, server, etc.) after transformative processing engine 108 receives the message, that node can report back to transaction management engine 106 that it saw the message. In this manner, transaction management engine 106 may enable end-to-end tracking of messages for the life of the message.

In one example, the messages are requests. The requests may be generated based on user input at one of the components. The requests may be received by transformative processing engine 108 and integrated into the system. In some examples, transaction management engine 106 may be notified that the requests have been received and may therefore be configured to generate message IDs for each request. These message IDs may then be associated with each of the requests. As the requests continue to move throughout the interaction system (e.g., away from transformative processing engine 108), transaction management engine 106 may be track their movement using the message IDs. If one of the requests does not make it to its destination, transaction management engine 106 (or part of the transaction management platform 528) may determine why the request was stopped. In some examples, this cause may be hardware related (e.g., an unplugged Ethernet cable, a broken router, etc.), software related (e.g., a router routing to the wrong location), or any other reason for orders not arriving at their correct destination.

In some examples, transaction management engine 106 (e.g., transaction management collection engine 504 of transaction management engine 106) may receive the message and/or message identifier directly from one of components 410-418. For example, one of components 410-416 may be configured to generate the unique message identifier and/or communicate directly with transaction management engine 106. The message also may travel via one or more intermediate nodes on its way to the destination node. In some examples, a node is a component such as components 410-418, which may be running an application. In some examples, the unique identifier and the routing of the message to its destination may be stored in a table that also includes: a geolocation of each node, a network from which the message originated, a type of node, the unique node identifier, and a time associated with the message leaving the origination node. In some examples, transaction management collection engine 504 provides unique message identifiers to other elements of the interaction system to monitor the messages as they move throughout the interaction system. Transaction management collection engine 504 also provides a portion of the unique message identifiers to a transaction management platform (indicated by a circle 528) for further analysis of the message identifiers. Such analysis may include reconciliation of lost messages, latency reporting, audit management and compliance, and other such analyses.

As mentioned previously, interoperability engine 502 is configured to store data in data store 508. A plurality of sub-engines 510-516 of interoperability engine 502 are configured to perform operations relating to storing data in data store 508.

Interoperability engine 502 includes a tagging engine 510 configured to perform semantic tagging and indexing of data. Tagging engine 510 therefore is configured to receive data, read metadata associated with the data, semantically scan the content of the data, and associate one or more tags with the data. Tagging engine 510 may therefore have access to hundreds, thousands, or even more possible tags. These tags may have been input by users, learned, pre-defined, generated by outside third-party mapping sources, and/or gathered from other components and/or data stores of the interaction system. For example, if the data is a chart for an entity, the tagging engine may be configured to read any metadata associated with the chart to determine which tags may be appropriate to associate with the chart. From the metadata, tagging engine 510 may determine that the chart is for a type of entity by reading metadata indicating that an author field is populated with the name of another particular type of entity. Tagging engine 510 may have access to other data to compare the analyzed metadata against (e.g., to identify that the author's name corresponds to Dr. Brown who is an oncologist). Other examples, of metadata that may be included in one or more fields include author, document type, creation time and date, last update time and date, upload time and data, geographic location, unique ID associated with the client or facility where the data originated, and other similar fields. The tags may be stored in association with the data (e.g., the chart) and/or may be stored independent from the data but include an identifier such that when searching tags the data may be capable of population.

Continuing with the example from above, if the data is a chart for a first type of entity, tagging engine 510 may be configured to read the content of the chart to determine which tags may be appropriate to associate with the chart. For example, this may comprise analyzing the content of the chart (i.e., individual pages) semantically to look for artifacts (e.g., keywords, phrases, and the like) in the content. These artifacts may be identified by tagging engine 510 and used to decide which tags to associate with the document. In some examples, semantic scanning may involve filtering out words (e.g., articles, such as "a" and "the"), phrases, and the like. Similar to the reading of metadata, the tags may be pre-defined, user-defined, learned, and the like. In some examples, reading metadata associated with messages may provide meaning and/or give context to the particular record of data. This meaning and/or context may assist tagging engine 510 to determine one or more tags to associate with the data. The tags may be chosen, for example, based on values of particular fields in the data, detecting a frequency of one or more words in a document or metadata and/or of a set of related words (e.g., tagging a record with "cancer" upon detecting words such as tumor, metastasize, chemotherapy, radiation, oncology, malignant, stage 3, etc.). In this manner, tagging engine 510 may also index portions of the data within one or more data stores of data store 508. In some examples, such indexing may be based in part on the selected tags.

Interoperability engine 502 also includes a reports engine 512 configured to generate one or more reports or alerts based on data. For example, reports engine 512 may generate reports when certain types of data are received or when data with certain characteristics is received. Reports engine 512 may also generate alerts. The reports and/or alerts generated by reports engine 512 may be outputted in the form of one or more communications to an administrator, an authorized user, or other similar user via a user device. Such communications can include, for example, signals, sirens, electronic notifications, popups, emails, and the like. Content of such communications may include information characterizing a performance metric, efficiency and/or outcomes; identifying concerning patterns; identifying losses of data; and the like. In some examples, the content is presented in the form of one or more documents, tables, figures, charts, graphs, and the like.

Interoperability engine 502 also includes a rules engine 514 configured to create and manage business rules, condition-response rules, alert/reports rules, data-formatting rules, data-sharing rules, transmission rules, aggregation rules, user authorization rules, and other similar rules. Such rules may be user-defined, fixed, learned by elements of the interaction system, and any combination of the foregoing. Finally, interoperability engine 502 includes an application engine 516 configured to provide service-oriented architecture web services.

Data store 508 includes an electronic record information data store 518 ("record data store 518"), a general data store 520, an operational data store 522, an entity-based data store 524, and a streaming caching storage 526. While data store 508 is illustrated as including a fixed number of data stores and storage elements, it is understood that data store 508 can include any suitable number of data stores and storage elements, including more than illustrated or less than illustrated.

In some examples, a data query script is provided to query a first data store and/or to obtain data for populating a data store. Such script could query a data store described herein (e.g., data store 508) and/or could be used to obtain data to populate a data store described herein (e.g., data store 508). In one instance, the script is configured to be repeatedly executed, so as to repeatedly draw data from a source data store. The retrieved data can then be formatted, filtered, sorted and/or processed and then stored, presented and/or otherwise used. In this manner, the script can be used to produce streaming analytics.

In some instances, the data query script, when executed, identifies each of the data stores of interest. Identifying the data stores of interest involves identifying at least a portion of data from the data stores simultaneously and/or sequentially. For example, the script can identify corresponding data stores (e.g., or components of a single data store or multiple data stores) that pertain to one or more similar variables but that differ in one or more other variables. Once the portion of the data from the data stores is identified, a representation of the identified data can be output to one or more files (e.g., Extensible Markup Language (XML) files) and/or in one or more formats. Such outputs can then be used to access the data within one or more relational database accessible using Structured Query Language (SQL). Queries made using SQL can be made sequentially or in parallel. Results from an SQL query may be stored in a separate database or in an XML file that may be updated either in part or as a whole. The data query script may be executed periodically, in accordance with a user-defined rule, in accordance with a machine-defined or machine-learned rule, and in other suitable manner.

[Within record data store 518 is retained data including electronic record information. In some examples, the information within record data store 518 is organized according to entity identifying information. Thus, record data store 518, in some examples, includes individually identifiable information. But it may also include de-identified information.

Within general data store 520 is retained data. The data may be stored in a relational database format or in any other suitable format. Thus, the data within general data store 520 may be retained in a data structure that includes one or more tables capable of accessing each other. In some examples, general data store 520 includes a subset of the information that is included in operational data store 522.

Within operational data store 522 is retained data in a relational database format. Thus, the data within operational data store 522 may be retained in a data structure that includes one or more data structures (e.g., tables) capable of accessing each other. Operational data store 522 is an example of an operational data warehouse. In operational data store 522 is joined many different types of data. F2. In some examples, the operational data ware house 522 includes data pertaining to decision making as discussed herein and other data typically used by conventional business concerns.

Within entity-based data store 524 is retained data in a non-relational database format. Thus, the data within entity-based data store 524 may be retained in a structure other than tables. Such structure may be appropriate for large and complex data sets. In some examples, entity-based data store 524 (or any other data store) may be a unified system, which may include: a document-centric, schema-agnostic, structure-aware, clustered, transactional, secure, database server with built-in search and a full suite of application services. An example of such a unified system may be Marklogic. Entity-based data store 524 can support data aggregation, data organization, data indexing, data tagging and mapping to semantic standards, concept matching, concept extraction, machine learning algorithms, concept discovery, concept mining, and transformation of personal record information. In some examples, entity-based data store 524 includes data pertaining to decision making (similar to general data store 520) as discussed that is organized and accessed in a different manner. For example, the data within entity-based data store 524 may be optimized for providing and receiving information over one or more information exchanges. In some examples, entity-based data store 524 includes a subset of the information that is included in operational data store 522.

Finally, in some examples, streaming caching storage 526 is a streaming data cache data store. As discussed previously, certain components of components 410-418 may support streaming data to other components or user devices. Streaming caching storage 526 is a location where streaming data can be cached. For example, assume that component 418 is a piece of equipment operating at Location A and that a user using a computer in Location B desires to view a live of substantially live stream of outputs of the piece of equipment. Component 418 can send a portion of data to streaming caching storage 526 which can retain the portion of the data for a certain period of time (e.g., 1 day). Thus, streaming caching storage 526 is configured to cache data that can be streamed.

Diagram 500 also includes data store integrity engine 506. In some examples, data store integrity engine 506 is configured to ensure integrity of the information within data store 508. For example, data store integrity engine 506 applies one or more rules to decide whether information within all or part of data store 508 should be scrubbed, removed, or adjusted. In this manner, confidence is increased that the information within data store 508 is accurate and current.

Figure 6:
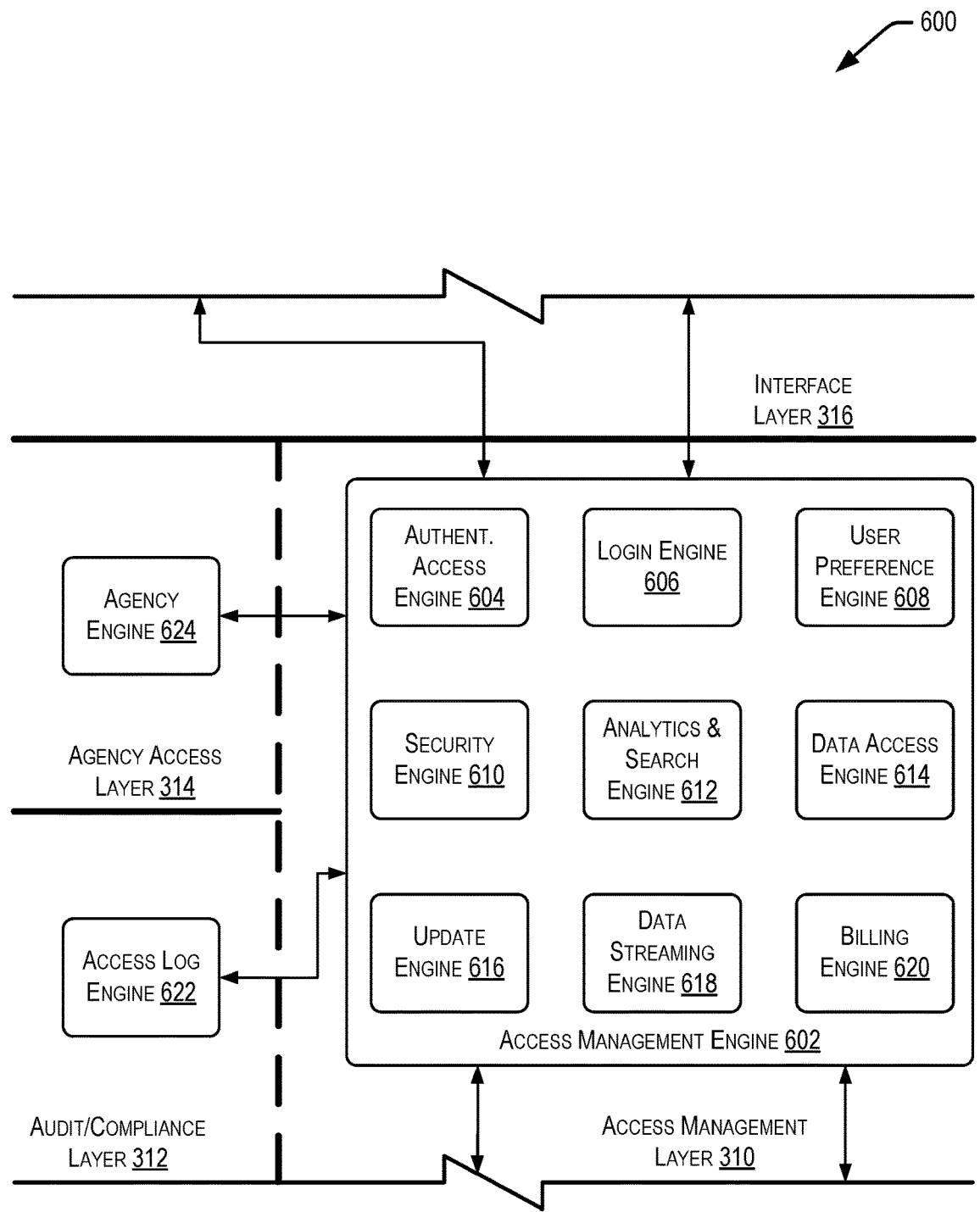
FIG. 6 is an example schematic model illustrating an aspect of the network communication model of FIG. 3 in more detail.

FIG. 6 shows a diagram 600 which depicts a portion of architecture stack 300 according to an embodiment of the invention. In particular, the diagram 600 includes access management layer 310, audit/compliance layer 312, agency layer 314, and a portion of interface layer 316.

Access management layer 310, as illustrated in the diagram 600, includes an access management engine 602. Access management engine 602 is an example of access management engine 222. Generally, access management engine 602 can be configured to manage access to elements of transformative processing engine 202 by different components, applications, and user devices.

Access management engine 602 within access management layer 310 also provides functionality similar to an operating system. For example, access management engine 602 includes a plurality of engines configured to manage different aspects of interacting with elements of the interaction system. For example, a user who desires to access portions of data retained in data store 508, may do so by interacting with access management engine 602 using one or more applications (not shown). Thus, access management engine 602 includes a variety of engines to enable such interaction. The engines include, for example, an authentication access engine 604, a login engine 606, a user preference engine 608, a security engine 610, an analytics and search engine 612, a data access engine 614, an update engine 616, and a streaming data engine 618. The different engines of access management engine 602 can define routines, protocols, standards, and the like for interacting with elements of the interaction system.

Beginning first with authentication access engine 604, authentication access engine 604 evaluates the rules and conditions under which users may access elements of the interaction system; in particular, the conditions under which users may access data within data store 508. These rules and conditions may be user-defined (e.g., by an administrator or reviewer), learned over time, and/or may be dynamically updated and/or evaluated based on characteristics of the user or the user's device attempting to access the interaction system. The rules and conditions may indicate the types of users who have particular types of access within the interaction system. The type of access may also relate to the degree to which data is identified/de-identified. In some examples, a user desiring access to data provides certain identifying information and authentication access engine 604 authenticates an identity of the user.

Login engine 606 evaluates the rules and conditions under which users are able to log in to the interaction system or access applications associated with the interaction system. These rules and conditions may be user-defined (e.g., by an administrator), learned over time, and also may be dynamically updated and/or evaluated based on characteristics of the user or the user's device attempting to access the interaction system. Thus, while authentication access engine 604 evaluates the rules to determine which users may access the interaction system, login engine 606 evaluates the particular credentials, profiles, etc. of the users. For example, login engine 606 can confirm that an entered username (e.g., and password), provided biometric data or code or identifier in a scanned tag or badge matches that in an authorized user data structure.

Login engine 606 evaluates one or more user profiles associated with each authenticated user. In some examples, a user profile includes a username, password, and other information associated with the user. For example, a user profile may indicate characteristics about the user.

User preference engine 608 evaluates the rules and conditions under which user are able to store and update one or more user preferences corresponding to access of the interaction system or access to applications associated with the interaction system. These rules and conditions may be user-defined (e.g., by the user or administrator), and may include rules for default preferences. For example, using user preference engine 608, a user may indicate a format in which the user prefers to receive outputted information, display characteristics of a graphical user interface associated with the user, and other similar user preference settings. For example, the user may indicate that certain types of reports and/or alerts are to be sent to the user.

Security engine 610 evaluates the rules and conditions for ensuring the security of access to the elements of the interaction system. In some examples, these rules and conditions are determined by administrators of the interaction system. In some examples, security engine 610 provides a plurality of computer virus protection services. These services can be called up and implemented when accessing the interaction system or accessing applications associated with the interaction system. The rules and conditions may be based on roles, based on profiles, based on domains, and any other suitable security configuration. For example, because the interaction system may include sensitive data, security engine 610 may enforce a domain-based rule that protects certain sensitive information (e.g., identifying information).

Analytics and search engine 612 evaluates the rules and conditions under which users can search for data within the interaction system and access analytics relating to the interaction system. In some examples, these rules and conditions are user-defined or learned over time in accordance with search engine optimization techniques. For example, analytics and search engine 612 is used to search within data store 508 for particular data. Analytics and search engine 612 supports any conventional searching algorithms. For example, search engine 612 can be used to search within various fields and potential field values. In some examples, search engine 612 can provide analytics, such as statistics, graphs, distributions and/or comparative analysis pertaining to particular entities and/or characteristics. Such information may be selected by a user and presented on a user interface.

Data access engine 614 evaluates the rules and conditions under which users may operation in order to access particular data within data store 508. In some examples, these rules and conditions are user-defined or learned over time. For example, data access engine 614 may indicate the routines, subroutines, or other logic needed for an application to access certain portions of data store 508. For example, while authentication access engine 604 and login engine 606 may manage which users can access parts of the interaction system, data access engine 614 may manage how authenticated users access data within data store 508. To this end, data access engine 614 may enforce and/or evaluate certain rules managing how users access different components of the interaction system. In some examples, data access engine 614 may be used to actually access data within data store 508 (e.g., extract, download, or otherwise access). In some examples, data access engine 614 may define procedures, protocols, and the like for accessing data. The protocols and procedures for accessing data access engine 614 (like the other engines of access management engine 602) may be provided to developers in the form of a software development kit (SDK). SDKs may enable developers write applications that can effectively communicate with elements (e.g., data store 508) of the interaction system. In particular, applications that can access a portion of the data stored within active unified data layer 308.

Update engine 616 evaluates the rules and conditions for providing updates to other engines within access management engine 602, plug-ins for applications that access the interaction system, and for other similar elements of the interaction system. For example, updates may be generated at runtimes, at defined time intervals, upon request by a user, upon receiving a threshold quantity of new or changed data. Once an update is performed, an interface may be refreshed, a report may be sent indicating that the update was successful or unsuccessful, or the like.

Streaming data engine 618 defines the rules and conditions for enabling streaming of data between components and user devices of the interaction system. For example, streaming data engine 618 may enable component 414 to stream data. Streamed data may include live or substantially live audio or video feeds, results of tests, output from equipment or devices, and any other suitable type of data capable of being streamed. In some examples, the data may be streamed to other components or user devices within the network or outside the network. In order to establish a streaming transmission, streaming data engine 618 may identify a streaming destination and a streaming origin. Next, streaming data engine 618 may pair the two and enable streaming. This may include allocated bandwidth within one or more network devices associated with the interaction system. Streaming data engine 618 may also adjust the quality of the streaming data based on the availability of bandwidth. In some examples, streaming data engine 618 may receive incoming streams (and continuously present the stream or monitor for particular data (e.g., exceeding a threshold, exhibiting an above-threshold change, having a particular value)).

Within audit/compliance layer 312 is located an access log engine 622. Access log engine 622 evaluates the rules and conditions for logging access to the interaction system by users, applications, devices, and the like. Logging access includes, in some examples, logging data conventionally collected by access log engines running in similar environments. Access log engine 622 can use this data to generate and transmit reports, for example, to stakeholders of the interaction system such that they can make informed decisions regarding that is accessing the interaction system and for what purposes.

Within agency layer 314 is located an agency engine 624. Agency engine 624 evaluates the rules and conditions under which agencies can access the interaction system. For example, agencies that may use agency engine 624 include agencies to which the interaction system provides compliance, tracking, or other reporting information. For example, agency engine 624 may be used to track one or more performance indicators identified by a government agency and/or to provide report instances of defined types of events. Thus, in some examples, a government agency uses agency engine 624 to collect data pertaining to compliance of the interaction system with one or more statutes or regulations. In some examples, a university is an agency that uses agency engine 624 to collect data pertaining to one or more studies. In some examples, agency engine 624 can identify one or more entities (e.g., governmental agencies) that are to receive reports pertaining to operations or events and what types of data are to be reported to those entities. Agency engine 624 can then collect the pertinent data, potentially format and/or analyze the data, and facilitate transmission of (e.g., raw, formatted and/or analysis of) the data to the appropriate agency.

Figure 7:
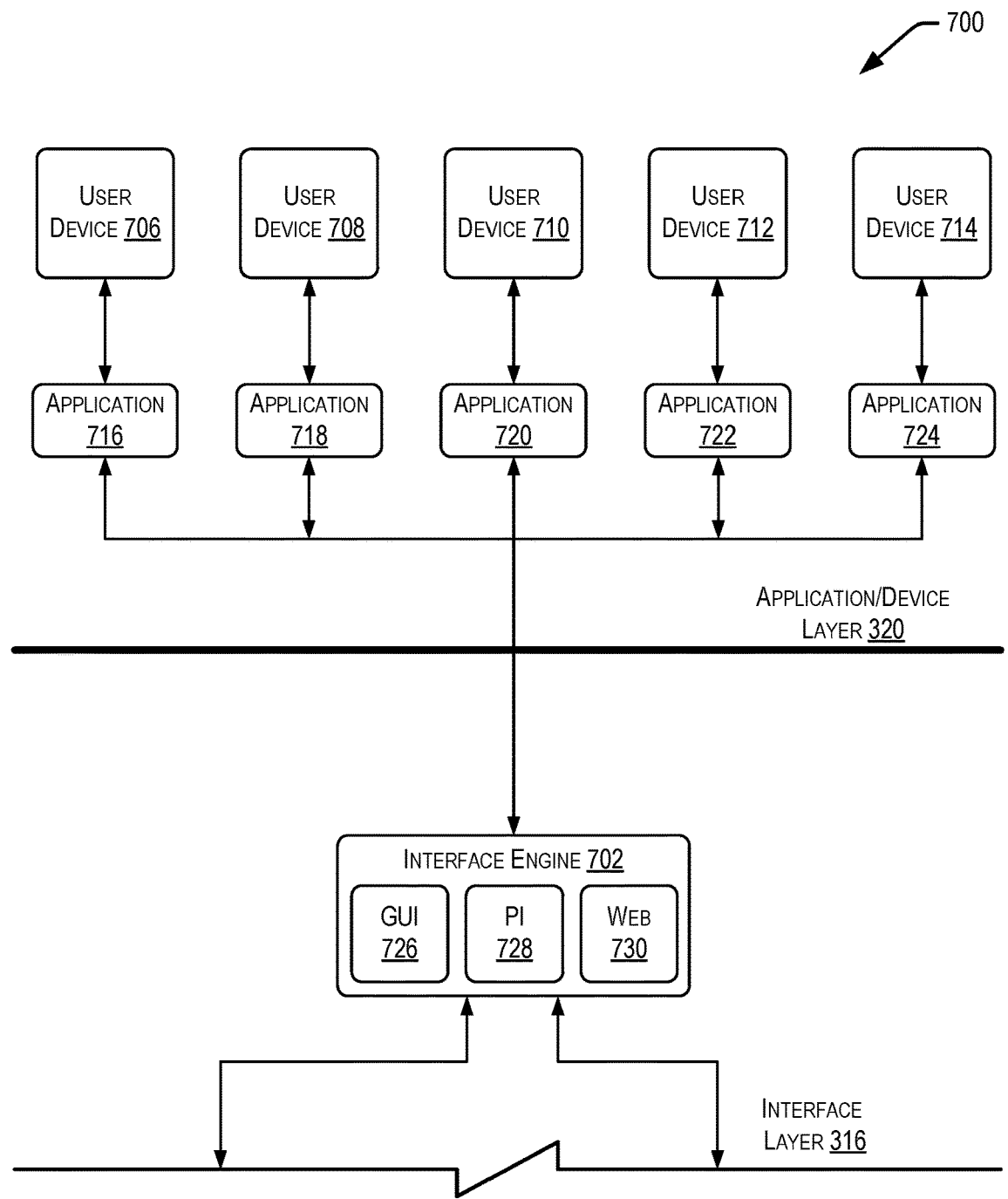
FIG. 7 is an example schematic model illustrating an aspect of the network communication model of FIG. 3 in more detail.

FIG. 7 shows a diagram 700 which depicts a portion of architecture stack 300 according to an embodiment of the invention. In particular, diagram 700 includes interface layer 316, and application/device layer 320. Within interface layer 316 is located interface engine 702 (e.g., interface engine 224). Interface engine 702 is configured to generate one or more interfaces (e.g., graphical user interface 726, programmatic interface 728, and/or web interface 730) to enable data to flow to user devices 710, 712, and 714 via respective applications 720, 722, and 724. In some examples, the interfaces of interface engine 702 are embodied in hardware, software, or some combination of both. Within interface layer 316 communications and inputs directed to interacting with elements of access management layer 310 may be embodied.

Graphical user interface 726 is any suitable graphical user interface configured to interact with elements of the interaction system. Programmatic interface 728 includes an application programming interface, a programmatic user interface, and other similar interfaces for defining core functions for accessing elements of the interaction system. For example, programmatic interface 728 may specify software components in terms of their operations. Web interface 730 is any suitable web interface configured to interact with elements of the interaction system. Any of the interfaces described herein may be configured to receive user input, present dynamic presentations that depend on user input, and otherwise respond to user input. In some examples, such input may be provided via one or more input devices (e.g., a keyboard, touchscreen, joystick, mouse, microphone, devices capable of capturing inputs, and the like) operated by one or more users of user devices 706-714. Output may be provided via one or more output devices (e.g., a display or speaker).

Interface engine 702 is utilized by applications internal to the interaction system and external to the interaction system to access data. In some examples, the applications that are internal include applications that are developed for internal use by various entities associated with the interaction system. In some examples, the applications that are external to the interaction system include applications that are developed for external use by those that are not associated with the interaction system.

Generally, within application/device layer 320, applications 716-724 which communicate with other elements of architecture stack 300 using the interfaces generated by interface engine 702 are defined. This includes detailing how applications 716-724 are to interact with the interfaces generated by interface engine 702 for accessing data. For example, interacting may include accepting inputs at user devices 706-714 to access data and, in response, providing the data, prompts, or other types of interaction with one or more users of the user devices 716-714. Thus, applications 716-724 may be related to one or more of the interfaces generated by interface engine 702. For example, application 720 may be interact with a graphical user interface (whether generated by interface engine 702 or otherwise) to interact with other elements of the interaction system. Interacting may include receiving inputs at the graphical user interface via application 720, providing output data to the graphical user interface application 720, enabling interaction with other user devices, other applications, and other elements of the interaction system, and the like. For example, some of the inputs may pertain to aggregation of data. These inputs may include, for example, types of data to aggregate, aggregation parameters, filters of interested data, keywords of interested data, selections of particular data, inputs relating to presentation of the data on the graphical user interface, and the like. Providing output data may include providing the aggregated data on the graphical user interface, outputting the information to one of the other user devices 706-714 running one of the other applications 716-724.

Turning now to the details of applications 720, 722, and 724. In some examples, applications 720, 722, and 724 include a variety of different applications that can be designed for particular users and/or uses. In one example, application 720 includes dashboards, widgets, windows, icons, and the like that are customized for an particular entity. In some examples, application 720 may present different data depending on a specialty associated with the entity and protected information associated with the entity. In this manner, application 720 adapts and automatically adjusts depending on the context in which the entity is using the application. In some examples, the data indicates performance statistics for the entity, metrics relating to where the entity falls along a distribution of other similar entities, outlier instances, trends in events or actions, and the like. Application 720 may be configured to receive input, adjust presentations, present unpromopted alerts, adjust display of content, move more relevant content to the foreground, move less relevant content to the background, populate forms for the entity.

In another example, application 722 may be specific for nurses or types of nurses. In this example, application 722 may include dashboards, widgets, windows, icons, and the like that are customized to individual nurses. Similar to the example discussed above pertaining to the doctor, in some examples, application 724 may present different data depending on a position of the nurse. In this manner, application 722 adapts and automatically adjusts depending on the context in which the nurse is using the application. For example, the nurse may receive data, such as test results.

In some examples, application 724 may be a multi-role application for administrators and is used to manage entities constitute the population of the entities or organizations within the interaction system. Similar to the other examples discussed, in some examples, application 724 may present different data depending on a role of the user who is using application 724. In this manner, application 724 adapts and automatically adjusts depending on characteristics of the user who is using application 724. In this manner, application 724 can provide different data depending on the role of the user. For example, whether data presented includes identifiable or de-identified information may depend on a position of the user.

In some examples, application 724 may be a business intelligence application. In this example, application 724 is used to display business information generated by components of the interaction system. This business information can be used for operations, planning, and forecasting. Such business information may include data because such data may impact operations, planning, forecasting, and the like. Accordingly, application 724 may present de-identified information in the form of one or more metrics, indicators, or the like as they pertain to business intelligence.

Applications 716 and 718 shown in connection with interface engine 702 are applications developed by third-parties. In some examples, such applications include any suitable application that benefits from accessing data. The interaction system may include data pertaining to hundreds of thousands of entities. Having data pertaining to so many entities presents security concerns. For example, much of the data may be identifying data. Accordingly, data that may be accessed by applications 716 and 718 may be limited. In some examples, an entity of the interaction system may use one of applications 716, 718 to access his or her own data. In this example, the identity of the entity may be verified in accordance with techniques described herein.

User devices 706-714 are any suitable user devices capable of running applications 716-724. User devices 706-714 are examples of the user device 228. In some examples, the user devices include: mobile phones, tablet computers, laptop computers, wearable mobile devices, desktop computers, set-top boxes, pagers, and other similar user devices. In some examples, at least some of user devices 706-714 are the same devices as at least some of the one or more components 410-418. In some examples, user devices 706-714 may include complementary layers to application/device layer 320 and/or receiving layer 302. For example, user devices 706-714 may include a transmission layer, a generation layer, and/or a receiving layer to communicate data at application/device layer 320 and at receiving layer 302.

Figure 8:
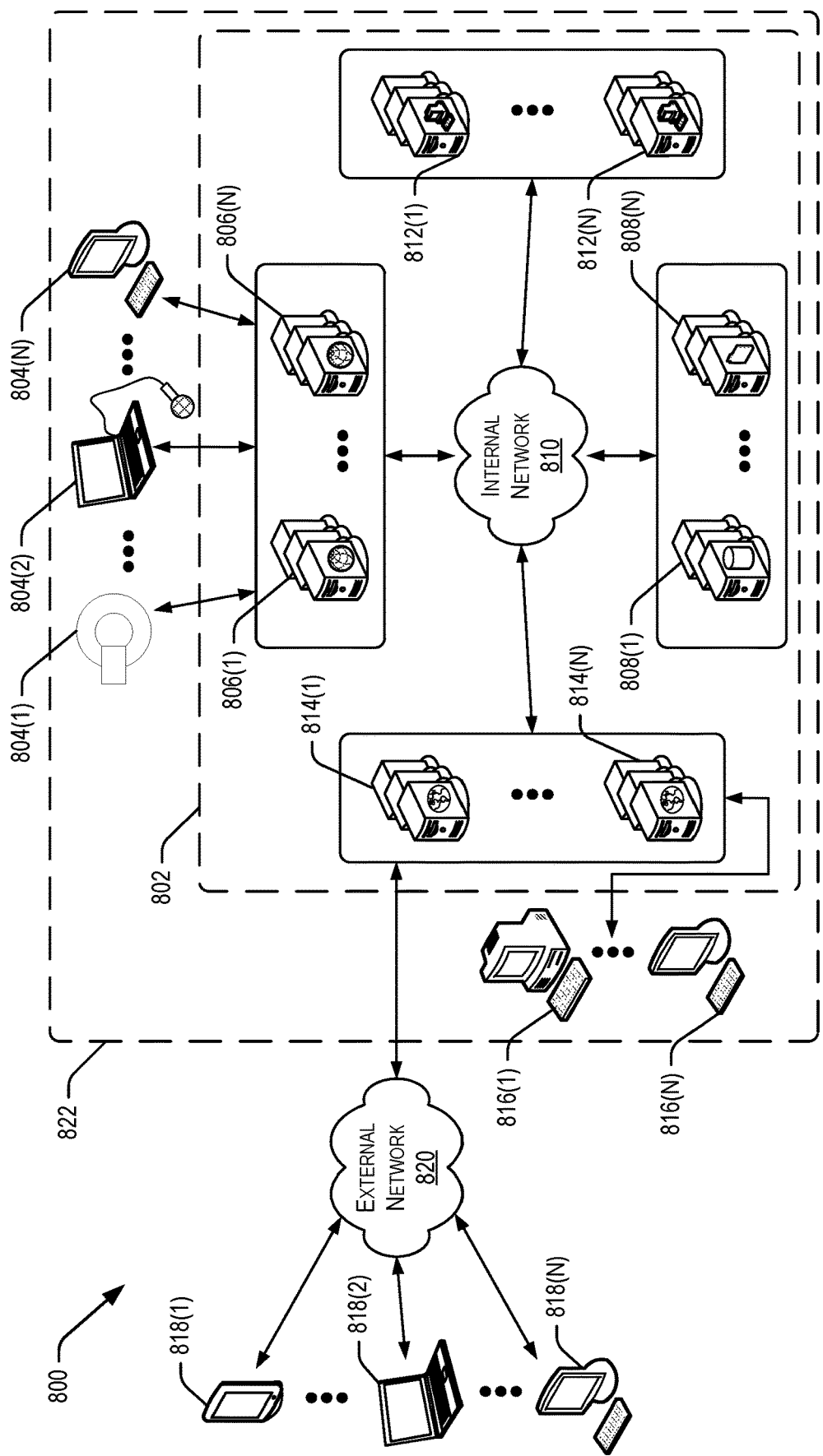
FIG. 8 is an example schematic architecture illustrating a network in which techniques relating to generating contextual suggestions and providing contextual suggestions to authorized users as described herein may be implemented, according to at least one example.

Turning now to FIG. 8, an interaction system 800 is shown in accordance with an embodiment of the invention. Interaction system 800 includes an internal organization 822 including a transformative processing engine 802. The transformative processing engine 802 is an example of transformative processing engine 202 previously discussed. Interaction system 800 is illustrated as an example configuration for implementing the techniques described herein. In particular, a configuration of elements as illustrated in FIG. 8, at least in some examples, communicates according to the layers of architecture stack 300. For example, internal organization 822 includes generation components 804(1), 804(2), and 804(N) which provide data to aggregation servers 806(1)-806(N).

Generation components 804(1), 804(2), and 804(N) operate in accordance with receiving layer 302. In some examples, generation component 804(1) is a piece of equipment, generation component 804(2) is computer with a data collection device, a type of lab system, and generation component 804(N) is a terminal. Aggregation servers 806 (1)-806(N) operate in accordance with aggregation layer 304. Aggregation servers 806(1)-806(N) share data with data storage servers 808(1)-808(N) via one or more internal network(s) 810. In some examples, internal network 810 is any suitable network capable of handling transmission of data. For example, internal network 810 may be any suitable combination of wired or wireless networks. In some examples, internal network 810 may include one or more secure networks. Data storage servers 808(1)-808(N) are configured to store data in accordance with active unified data layer 308. Data storage servers 808(1)-808(N) include database servers, file storage servers, and other similar data storage servers.

Access management servers 812(1)-812(N) manage access to the data retained in the data storage servers 808(1)-808(N). Access management servers 812(1)-812(N) communicate with the other elements of interaction system 800 via internal network 810 and in accordance with access management layer 310.

Interface servers 814(1)-814(N) provide one or more interfaces applications to interact with the other elements of interaction system 800. Interface servers 814(1)-814(N) provide the one or more interfaces and communicate with the other elements of interaction system 800 via internal network 810 and in accordance with interface layer 316. The interfaces generated by the interface servers 814(1)-814(N)

can be used by internal user devices 816(1)-816(N) and external user devices 818(1), 818(2), and 818(N) to interact with elements of interaction system 800.

Internal user devices 816(1)-816(N) are examples of user devices 706-714. In some examples, internal user devices 816(1)-816(N) run applications via the interfaces generated by interface servers 814(1)-814(N). As an additional example, external user devices 818(1), 818(2), and 818(N) can run applications developed by third parties that access the other elements of interaction system 800 via the interfaces generated by interface servers 814(1)-814(N).

External user devices 818(1), 818(2), and 818(N) access the interfaces via external network 820. In some examples, external network 820 is an unsecured network such as the Internet. External user devices 818(1), 818(2), and 818(N) are examples of user devices 706-714. External user device 818(1) is a mobile device. In some examples, the mobile device may be configured to run an application to access interaction system 800. Similarly, the other external user devices 818(2)-818(N) run applications that enable them to access interaction system 800. While interaction system 800 is shown as implemented using discrete servers, it is understood that it may be implemented using virtual computing resources and/or in a web-based environment.

Figure 9:
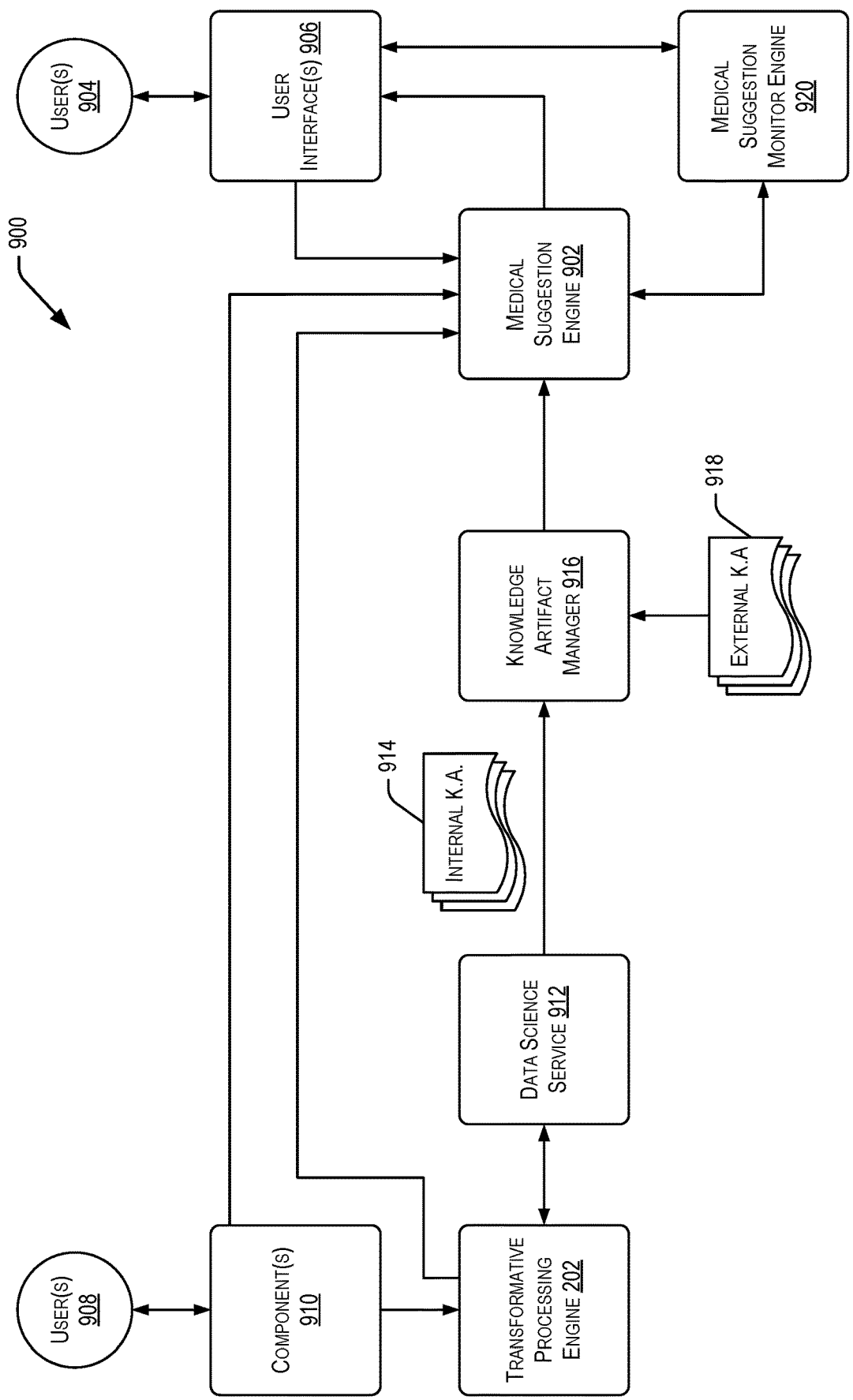
FIG. 9 is an example block diagram illustrating techniques relating to generating contextual suggestions and providing contextual suggestions to authorized users as described herein, according to at least one example.

Turning now to FIG. 9, a medical provider network 900 is shown in accordance with an embodiment of the invention. The medical provider network 900 may be implemented using at least some of the elements of the network 800. The medical provider network 900 includes a medical suggestion engine 902, which is configured to implement the techniques described herein. For example, the medical suggestion engine 902 generates medical decision support output (e.g., medical suggestions, recommendations, considerations, workflows parameters, and the like) that can be provided to receiving users 904 via one of more user interfaces 906. In order to generate the medical decision support output, the medical suggestion engine 902 receives certain medical-related information. The creation of such medical-related information begins with generation users 908. The generation users 908 and the receiving users 904 may come from the same group of users and may be similar to the users that operate the components 410-418 and/or the users that operate the user devices 706-714. Accordingly, the generation users 908 interact with components 910 to generate medical-related data. The components 910 are examples of the components 410-418 discussed herein.

The medical-related data generated by the users 908 interacting with the components 910 is provided to the transformative processing engine 202 and the transformative processing engine 202 performs one or more operations on the medical-related data such as those discussed herein. One of the operations includes the transformative processing engine 202 retaining the medical-related data in a manner that makes it searchable and useable by other elements of the medical provider network 900. For example, a data science service 912 interacts with the transformative processing engine 202 to access the medical-related data stored thereby. The data science service 912 analyzes the medical-related data retained by the transformative processing engine 202 to give the data meaning. For example, the data science service 912 evaluates the medical-related data to identify trends in the data or correlations between different data that could be valuable for treatment of patients of the medical provider network 900. Identified trends, correlations, and other outputs (e.g., evidence of treatment patterns, outcomes, and the like) identified from the medical-related data by the data science service 912 are referred to herein as internal knowledge artifacts 914 and are provided to a knowledge artifact manager 916. Other examples of the internal knowledge artifacts 914 include case studies of patients treated by medical care professionals associated with the medical provider network 900, results of internal medical journals, and other types of information that characterizes past medical treatment and that can be used to assist in future treatment of the same and/or similar patients.

The data science service 912 includes human users accessing computing devices to generate the internal knowledge artifacts 914. Generating the internal knowledge artifacts 914 may include adjusting relevant medical-related data into one or more formats, particular data structures, or the like that can be read by the medical suggestion engine 902 when generating medical decision support output. A computing device of the data science service 912 may be any conventional computing device including a memory, processor, operating system, and the like for generating the internal knowledge artifacts 914. The data science service 912 may also include one or more automated engines within a computing device, or distributed throughout many computing devices. The engines may be configured to analyze the medical-related data and generate internal knowledge artifacts 914 programmatically. For example, the data science service 912 may include a learning engine that analyzes the medical-related data to identify trends, correlations, patterns, and the like in a similar manner as the human users described above. The internal knowledge artifacts 914, whether generated with the assistance of human users or generated programmatically, are provided to the knowledge artifact manager 916 that manages the internal knowledge artifacts 914. This may include organizing the internal knowledge artifacts 914 in a manner useable by the medical suggestion engine 902. To this end, the knowledge artifact manager 916 may include a memory, which may be distributed among many different devices.

The knowledge artifact manager 916 also receives external knowledge artifacts 918. The external knowledge artifacts 918 are generated by organizations, users, and others that fall outside of a medical provider organization associated with the medical provider network 900. Thus, the external knowledge artifacts 918 may include medical journals, proprietary and non-proprietary medical-related data organized in some structure, research findings, medical theses, treatment patterns for patients with particular diagnosis, prescription drug characteristics, and any other suitable type of information that can be arranged and managed by the knowledge artifact manager 916. Thus, the external knowledge artifacts 918 and the internal knowledge artifacts 914 represent associations between certain medical situations (e.g., orders, diagnoses, etc.) and the medical outcomes in the related cases. In some examples, the knowledge artifact manager 916 is not included in the medical provider network 900 and the internal knowledge artifacts 914 and the external knowledge artifacts 918 are made available directly to the medical suggestion engine 902.

When the knowledge artifact manager 916 is included in the medical provider network 900, the knowledge artifact manager 916 manages all of the knowledge artifacts. To this end, the knowledge artifact manager 916 performs operations on the knowledge artifacts 914, 918 to retain them in the memory of the knowledge artifact manager 916 in a manner and format that is accessible by the medical suggestion engine 902. In some examples, once the knowledge artifact manager 916 receives the internal knowledge artifacts 914 and the external knowledge artifacts 918, the knowledge artifact manager 916 compares the different knowledge artifacts and may identify knowledge artifacts based on a combination of the internal knowledge artifacts 914 and the external knowledge artifacts 918. The knowledge artifact manager 916 receives the internal knowledge artifacts 914 and the external knowledge artifacts 918 on an ongoing basis. In some examples, the knowledge artifacts 914, 918 are sent to the knowledge artifact manager 916 periodically (e.g., hourly, daily, weekly, etc.), when requested by the knowledge artifact manager 916, in accordance with a user-defined rule or a machine-defined rule (e.g., send in batches consisting of ten knowledge artifacts), or in any other suitable manner. The knowledge artifact manager 916 in turn provides the knowledge artifacts 914, 918 to the medical suggestion engine 902 periodically, when requested by the medical suggestion engine 902, in accordance with a rule, or in any other suitable manner. In some examples, the medical suggestion engine 902 does not receive the knowledge artifacts 914, 918, but accesses them when needed.

In either case, the medical suggestion engine 902 accesses the knowledge artifacts 914, 918 and based on other current medical information, generates medical decision support output. The current medical information may be received by the medical suggestion engine 902 in real-time or substantially real-time. The current information is received from the transformative processing engine 202, the components 910, or via the user interfaces 906. The current information includes real world conditions data (e.g., social media feeds, news services, RSS feeds, information from organizations such as the Center for Disease Control, and the like that pertains to weather conditions, geographic health conditions, spread of diseases, and the like), details about a patient (e.g., medical record information), and details about a care scenario of the patient for which the medical suggestion engine 902 will make one or more suggestions. For example, the medical suggestion engine 902 may receive current information in the form of output from a dialysis machine (one of the components 910). The output may be associated with a particular patient of the medical provider network who was treated using the dialysis machine. The medical suggestion engine 902 accesses the output, which identifies the particular patient, and runs through a list of potentially-relevant knowledge artifacts that may assist the medical suggestion engine 902 in making a medical suggestion to the particular patient's doctor. For example, the medical suggestion engine 902 may determine that, based on a knowledge artifact (external, internal, or a combination) dealing with kidney failure, a prescription drug may be helpful for the particular patient. This information (i.e., recommended drug for the particular patient) is then provided to the doctor, who is one of the receiving users 904, as a medical suggestion. The medical suggestion is a type of medical decision support output that can be generated by the medical suggestion engine 902. The medical decision support output may therefore be based on the current information (e.g., real world conditions data, patient details, and care scenario details), knowledge artifacts, and output parameters and configuration settings (e.g., user-defined and machine-defined (e.g., learned) rules that define what output will be presented, how it will be presented, and other details about presentation).

The medical suggestion engine 902 may interact using the active unified data layer 308 or the access management layer 310. In some examples, at least a portion of the interactions of the medical suggestion engine 902 take place in the interface layer 316 and/or the application/device layer 320. In this manner, the medical suggestion engine 902 may be configured to provide the medical decision support output to the user interfaces 906. The user interfaces 906 are examples of the user interfaces capable of generation by the interface engine 702 and may be accessed by the receiving users 904 using applications running on user devices as described herein. The medical suggestion engine 902 provides the medical decision support output either by subscription or by publishing.

The medical provider network 900 also includes a medical suggestion monitor engine 920. The medical suggestion monitor engine 920 is configured to monitor the medical suggestion engine 902. This may include, for example, comparing medical decision support output (e.g., medical suggestions) generated by the medical suggestion engine 902 with result information characterizing whether medical care professionals acted on the suggestions, ignored the suggestions, or in some other way acknowledged the suggestions. Such result information is collected from the receiving users 904 via the user interfaces 906 or directly from users devices on which the receiving users 904 interact in some other way. In some examples, the result information is collected over time and provided to the medical suggestion monitor engine 920 periodically. In this manner, the medical suggestion monitor engine 920 may ensure that the suggestions generated by the medical suggestion engine 902 are current, correct, and meaningful. The medical suggestion monitor engine 920 is configured to adjust the weight of previously made medical suggestions if those suggestions are not being acknowledged. The medical suggestion monitor engine 920 also outputs reports, alerts, signals, and the like pertaining to medical suggestions. Such reporting may include recommendations to operators of the medical provider network 900 regarding adjustments to the medical suggestion engine 902, the knowledge artifact manager 916, the user interfaces 906, or any other element of the medical provider network 900.

Figure 10:
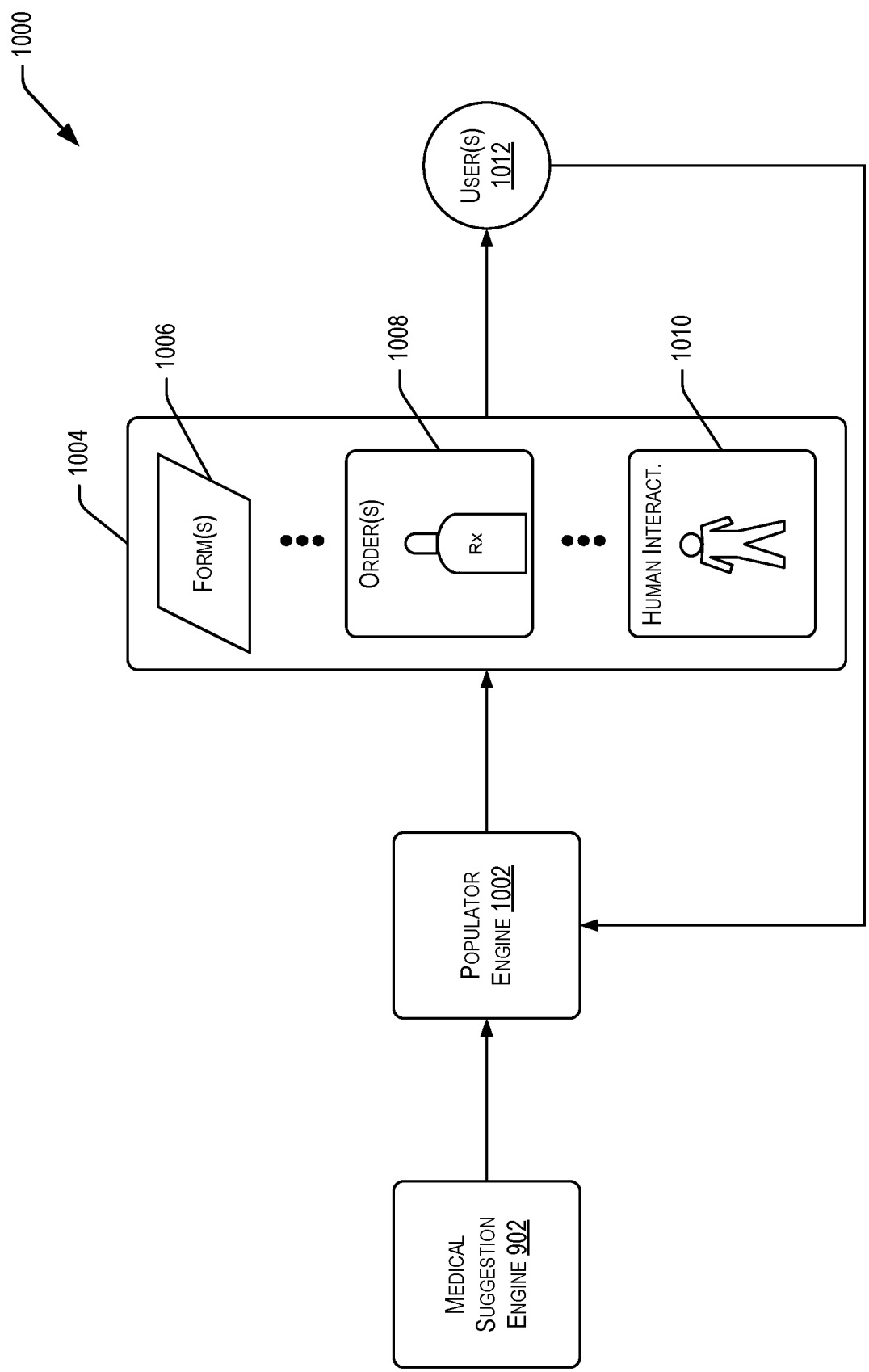
FIG. 10 is an example block diagram illustrating techniques relating to populating forms using contextual suggestions as described herein, according to at least one example.

Turning now to FIG. 10, a medical provider network 1000 is shown in accordance with an embodiment of the invention. The medical provider network 1000 includes the medical suggestion engine 902 and a populator engine 1002. In some examples, the populator engine 1002 is implemented as an engine within the medical suggestion engine 902 as discussed with reference to FIG. 9. In either case, after the medical suggestion engine 902 receives details about a course of treatment for a patient, it provides a list of possible medical tasks (e.g., a form of medical decision support output) to the populator engine 1002. The list of possible medical tasks are future medical tasks that are either recommended, suggested, and/or required for treatment of the patient. At least some of the future medical tasks may have corresponding medical forms, the submission of which are preconditions for fulfillment of the tasks. The populator engine 1002 therefore identifies from the medical tasks, a list of appropriate medical forms 1004. The list of medical forms 1004 may include any medical form that may be required prior to fulfillment of a medical task. For example, the list of medical forms 1004 may include medical forms 1006, medical orders 1008, and medical human interaction 1010. The medical forms 1006 are examples of forms for imaging, testing, lab work, and the like. The medical orders 1008 are examples of forms for prescriptions, treatment on particular medical devices, and the like. The medical human interaction 1010 are examples of forms for referrals to other medical care professionals, referrals to other medical care facilities, requests for consultations by specialists, discharge papers, check-in patient forms, and the like.

A list of medical forms 1004 is provided to users 1012. The users 1012 are examples of the generation users 908 and/or the receiving users 904. In some examples, the users 1012 receive the list and select which forms the populator engine 1002 should populate. In some examples, the populator engine 1002 populates all relevant forms from the list of medical forms 1004 and provides the list of pre-populated forms to the users 1012. Populating a form includes populating fields of the form using current information identified by the medical suggestion engine 902. The current information includes patient care scenario details and patient details, which may include identifying and non-identifiable personal health information. The populator engine 1002 is configured to protect personal health information and not present it to users that are not authorized to access it.

Figure 11:
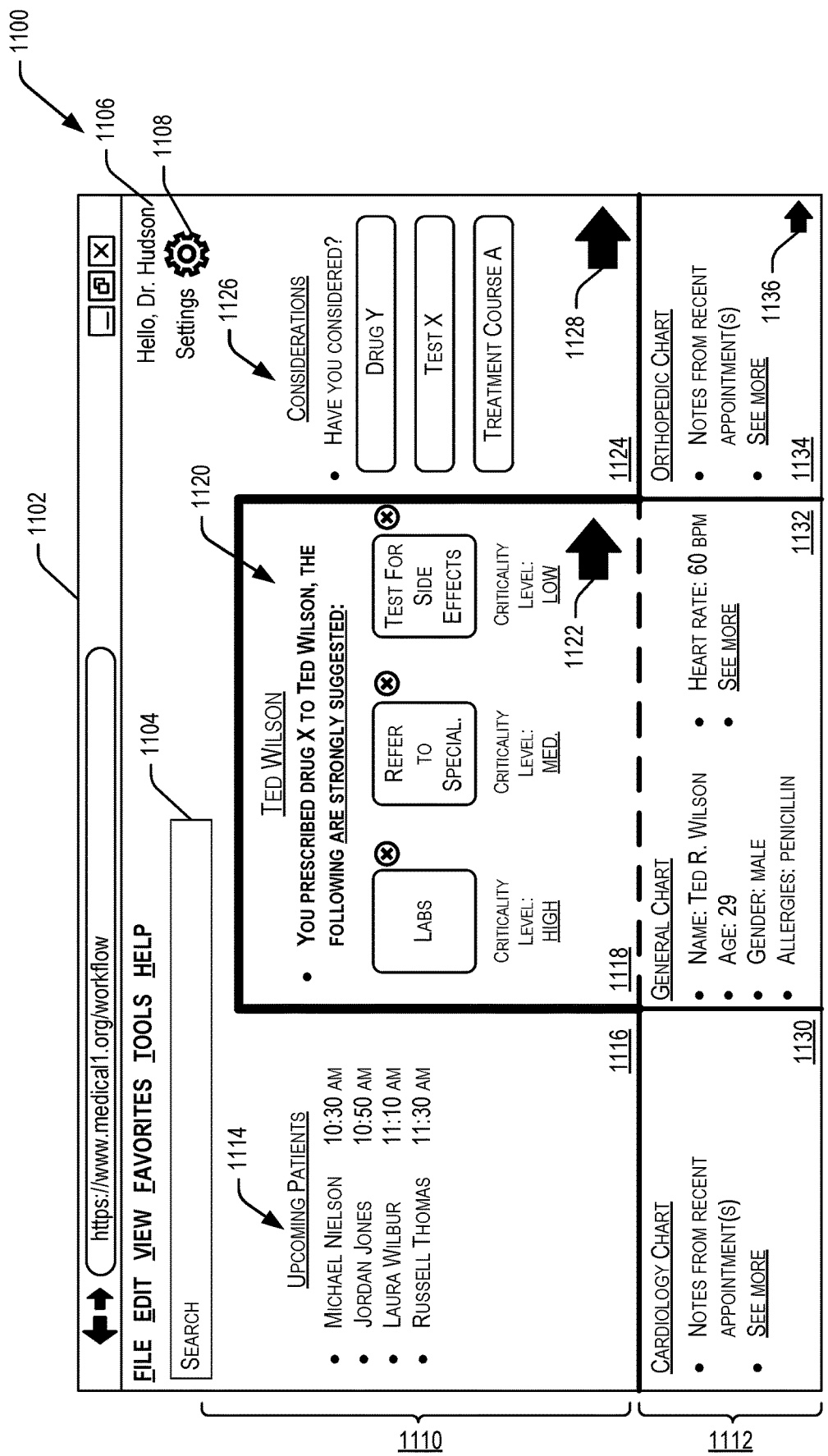
FIG. 11 is an example contextual user interface in which generated contextual suggestions may be provided to authorized users as described herein, according to at least one example.

Turning now to FIG. 11, a contextual medical user interface 1100 is shown in accordance with an embodiment of the invention. The contextual medical user interface 1100 is an example of the one of the user interfaces 906. Thus, in this example, the medical suggestion engine 902 provides medical decision support output to users via the contextual medical user interface 1100. The contextual medical user interface 1100 is illustrated as a webpage 1102. Thus, the contextual medical user interface 1100 in this example is a web interface. The webpage 1102 includes a search bar 1104 for searching within a medical provide network, the Internet, any other network, or within a database, data structure, or the like. The webpage 1102 also identifies Dr. Hudson 1106 as a medical care professional who has signed into the webpage 1102. Dr. Hudson 1106, or other user, may adjust the settings of how the webpage 1102 is configured and what information is presented by clicking on a settings icon 1108. Once Dr. Hudson 1106 adjusts the settings of the webpage 1102, the adjusted settings may be provided to the medical suggestion engine 902 to consider when making suggestions to Dr. Hudson 1106 via the webpage 1102.

The webpage 1102 includes workflow/suggestion area 1110 and patient chart area 1112. Within the workflow/suggestion area 1110 is presented patient list 1114 in area 1116. The patient list 1114 includes a list of patients that Dr. Hudson 1106 has on her schedule. The list includes "Ted Wilson" who Dr. Hudson 1106 is currently seeing. This may mean that Ted Wilson is being treated by Dr. Hudson 1106 or is waiting to be seen by Dr. Hudson 1106. The patient list 1114 also includes other patients that are on Dr. Hudson's 1106 schedule.

Adjacent to the area 1116, within the workflow/suggestion area 1110, and central to the webpage 1102 is area 1118. Within the area 1118 is presented medical suggestion information 1120. The medical suggestion information 1120 presented in the area 1118 includes medical suggestions that may be more critical than other medical suggestions. In other words, because the medical suggestion information 1120 is presented prominently in the center of the webpage 1102 (i.e., in the area 1118), Dr. Hudson 1106 may understand that the information presented here is important. In some examples, the medical suggestion engine 902 determines which medical suggestions should be presented based on a course of treatment. In this example, the medical suggestion information 1120 includes a sentence describing a course of treatment (i.e., "You prescribed drug X to Ted Wilson, the following are strongly suggested:") and a variety of medical tasks (i.e., "Labs" "Refer to Specialist," and "Test for Side of Effects") related to the course of treatment identified above. Clicking on a button that includes one of medical tasks (e.g., "Labs") may prompt the populator engine 1002 to identify and populate the appropriate forms for that medical task. In some examples, clicking the button provides additional information (e.g., medical journals, uses cases, availability, etc.) about the particular medical task. Each of the medical tasks include a criticality level as it relates to the course of treatment. For example, the medical task Labs includes a "high" criticality level. Because this information is presented to Dr. Hudson 1106, she can make an informed decision of whether to take the suggestion based on the context in which the suggestion is offered. In some examples, the medical suggestion information 118, including any medical suggestions described herein, may be determined and selectively presented based on the geographic location of the patient and/or the medical care professional (e.g., Dr. Hudson 1106).

Each of the medical tasks also includes an option to close out the suggestions. In some examples, this is considered an override of the suggestion and may be tracked by the medical suggestion monitor engine 920 for Dr. Hudson 1106, for the suggestion, for the course of treatment, and the like to learn how the suggestions are being considered. Additionally, Dr. Hudson 1106 can click arrow 1122 to reveal more suggestions relating to the identified course of treatment. In some examples, clicking the arrow 1122 may reveal other suggestions for other courses of treatment.

Adjacent to the area 1118 and within the workflow/suggestion area 1110 is area 1124. Within the area 1124 is presented medical consideration information 1126. The medical consideration information 1126 presented in the area 1124 includes medical considerations that may be less critical than the medical suggestions presented in the area 1118. It may be apparent that these medical considerations are less critical because they are presented off-center from the webpage 1102. The medical consideration information 1126 may include medical tasks related to the course of treatment or unrelated to the course of treatment. In some examples, the medical consideration information 1126 includes items that other doctors have considered when treating a patient similar (e.g., similar diagnosis, medical history, age, etc.) to Ted Wilson. Clicking on a button that includes one of medical tasks (e.g., "Drug Y") may prompt the populator engine 1002 to identify and populate the appropriate forms for that medical task. In some examples, clicking the button provides additional information (e.g., medical journal, uses cases, availability, etc.) about the particular medical task. Similar to the area 1118, the area 1124 includes arrow 1128. Clicking the arrow 1128 may reveal other medical considerations.

Below the workflow/suggestion area 1110 and within the patient chart area 1112 are areas 1130, 1132, and 1134. Generally, within the patient chart area 1112 is presented medical-related information from a medical record associated with Ted Wilson. In some examples, the medical record has been developed by different medical care professionals and may be organized according to specialty. Thus, within the area 1132 is presented general chart information. This information is associated with Ted Wilson, but general in the sense that almost any medical care professional would consider such information while treating Ted Wilson. To the left of the area 1132 is the area 1130. Within the area 1130 is presented cardiology chart information. This information also pertains to Ted Wilson, but may include certain entries that are specific for treatment by a cardiologist. Similarly, the area 1134 includes orthopedic chart information. In some examples, Dr. Hudson 1106 organizes the arrangement of information within the patient chart area 1112 by adjusting one or more settings associated with the contextual medical user interface 1100. In some examples, more or less chart information may be presented. By clicking arrow 1136, more types of chart information may be presented (e.g., neurology, oncology, etc.). In some examples, each of the areas 1130, 1132, and 1134 include a "see more" line. By clicking "see more," the contextual medical user interface 1100 is adjusted and more information is presented pertaining to the type of chart information. In some examples, any of the text on the webpage 1102 may be hyperlinked to present other content related to the linked text.

Figure 12:
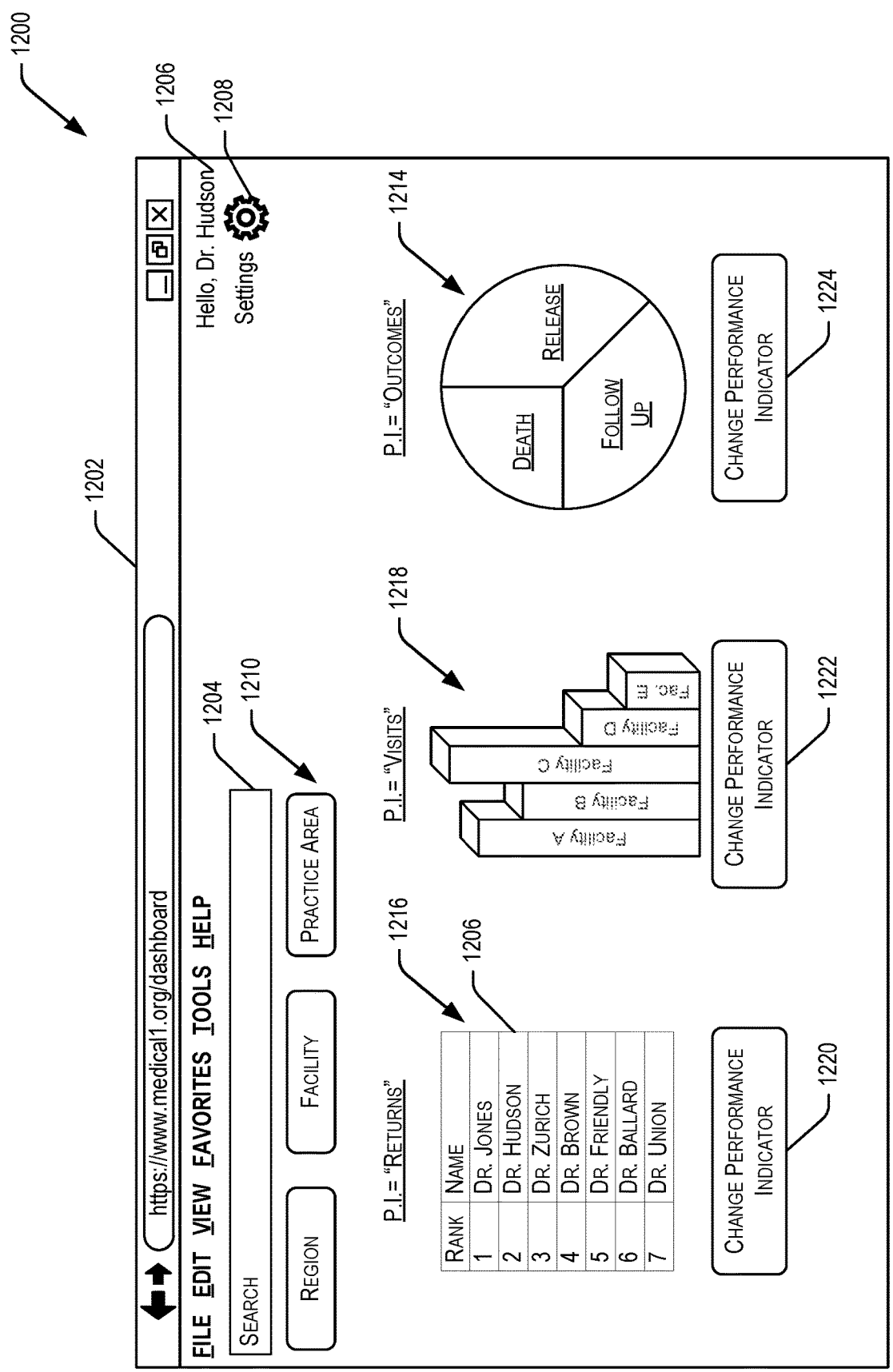
FIG. 12 is an example contextual user interface in which metrics related to authorized users may be presented and accessed as described herein, according to at least one example.

Turning now to FIG. 12, a medical analytics dashboard 1200 is shown in accordance with an embodiment of the invention. The medical analytics dashboard 1200 may be presented on one of the user interfaces 906. In some examples, the medical analytics dashboard 1200 is included as part of the contextual user interface 1100. The medical analytics dashboard 1200 is illustrated as a webpage 1202. The webpage 1202 includes a search bar 1204 for searching within a medical provide network, the Internet, any other network, or within a database, data structure, or the like. This may include searching medical analytics data, performance indicators, and the like. The webpage 1202 also identifies Dr. Hudson 1206 as a medical care professional who has signed into the webpage 1202. Dr. Hudson 1206, or other user, may adjust the settings of how the webpage 1202 is configured and what information is presented by clicking on a settings icon 1208. The webpage 1202 includes one or more filter criteria 1210 and one or more updateable graphical representations 1212. Clicking on one of the filter criteria 1210 may adjust what medical analytics data is presented by the updateable graphical representations 1212.

In some examples, the updateable graphical representations 1212 are presented as graphs, tables, or the like (e.g., in the form of application widgets) and organized based on medical care professional such as Dr. Hudson 1206. For example, for a particular medical performance indicator (e.g., "Outcomes"), the medical analytics data relating to this indicator is organized in a pie chart 1214 and presented in a way that informs Dr. Hudson 1206 of her own performance. The medical analytics data may also be presented in a way that compares medical care professionals according to the medical performance indicators. For example, for a particular medical performance indicator (e.g., "Returns"), the medical analytics data relating to this indicator is organized as a table 1216. Within the table 1216 is a ranking of medical care professionals, showing Dr. Hudson 1206 in the second position. The medical analytics data may also be presented in a way that compares medical care facilities according to the medical performance indicators. For example, for a particular medical performance indicator (e.g., "Visits"), the medical analytics data relating to this indicator is organized as a bar graph 1218. Within the bar graph 1218 is a comparison of medical care facilities. In some examples, such a comparison may be relevant to Dr. Hudson 1206 because Dr. Hudson 1206 practices at one of the facilities. Below each of the table 1216, the bar graph 1218, and the pie chart 1214 is a button (i.e., buttons 1220-1224) that can be selected to change the performance indicator. For example, selecting the button 1220 enables Dr. Hudson 1206 to change the performance indicator "Returns" to a different performance indicator (e.g., "Visits"). If done so, the table 1216 will be populated with medical analytics data pertaining to the indicator Visits.

Figure 13:
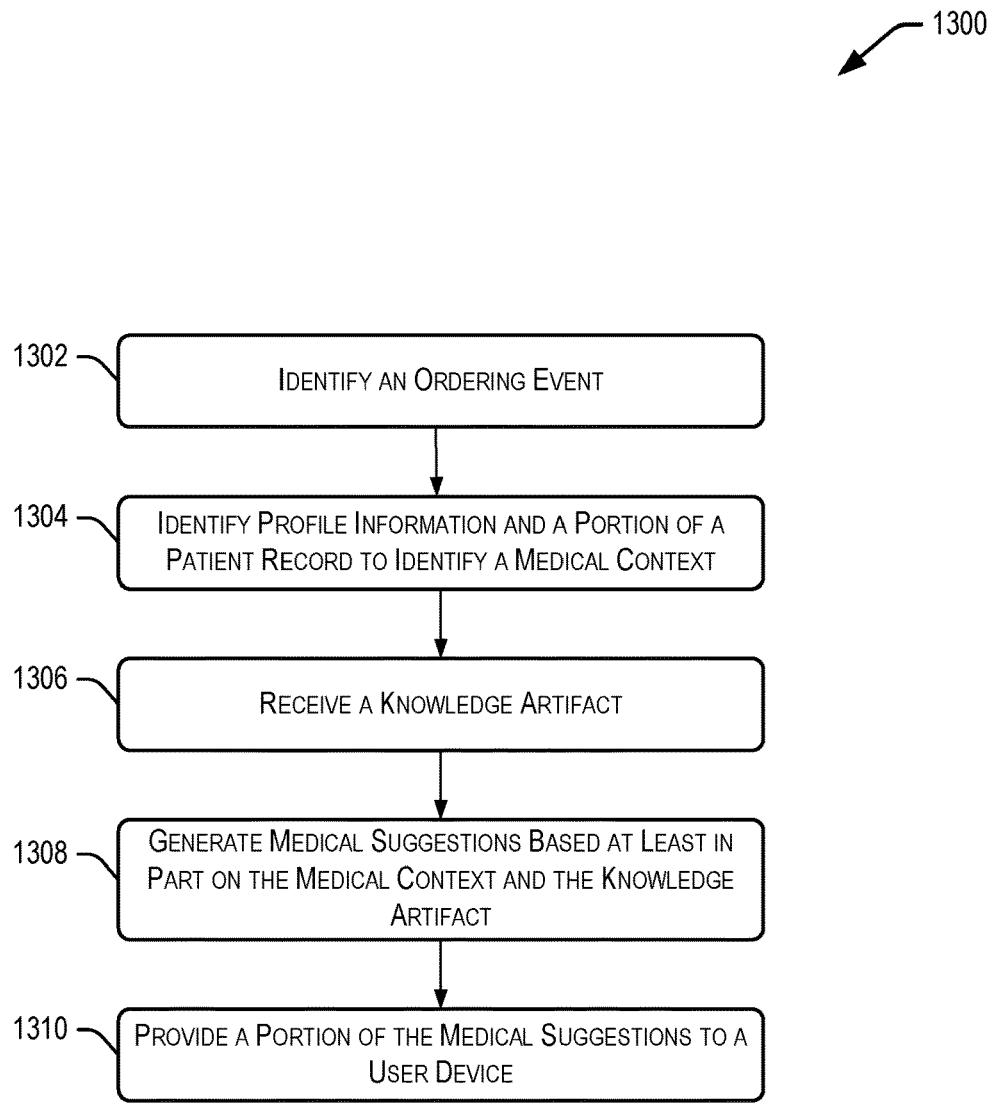
FIG. 13 is a flow diagram depicting example acts for implementing techniques relating to generating contextual suggestions and providing contextual suggestions to authorized users as described herein, according to at least one example.

FIG. 13 illustrates a flowchart of a process 1300 for generating a medical suggestion according to an embodiment of the invention. Some or all of the process 1300 (or any other processes described herein, or variations and/or combinations thereof) may be performed under the control of one or more computer systems (e.g., the medical suggestion engine 902, the transformative processing engine 202, the medical suggestion monitor engine 920, the populator engine 1002, or other system described herein) configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

The process 1300 begins at block 1302 by identifying an ordering event. The ordering event may correspond to a care scenario for a patient of a medical care professional. The ordering event may correspond to a decision point, an escalation event, and/or a communication event. The care scenario identifies details about the patient's care. For example, the care scenario may indicate a diagnosis, a treatment plan, a purpose for a visit to see the medical care professional, and the like. In some examples, the ordering event is any action initiated on behalf of the patient that affects the care scenario and/or medical care of the patient. For example, the ordering event may include the medical care professional (or other medical care professional) ordering a test for the patient, scheduling an appointment for the patient, reviewing a medical chart of the patient, prescribing a drug for the patient, providing a referral to the patient, requesting a consultation on behalf of the patient, recording a diagnosis of the patient in a medical record associated with the patient, and other similar event corresponding to the care scenario of the patient.

At 1304, the process 1300 identifies profile information and a portion of a patient record to identify a medical context. The profile information may correspond to the medical care professional and may include a medical profile. The medical profile includes details about the medical care professional, e.g., area of practice, geographic location, preferences, and the like. The medical patient record includes medical-related information that describes the patient and his or her medical history. Because the medical context is based on the profile information and the medical patient record, the medical context describes a context in which the medical care professional provides medical care to the patient. For example, the medical context may also be based on the care scenario of the patient. Thus, the medical context may describe who the patient is (i.e., the medical patient record), what diagnosis the patient has (i.e., the care scenario and/or the medical patient record), and who (i.e., the medical care professional) is treating the patient.

At 1306, the process 1300 receives a knowledge artifact. The knowledge artifact may be determined based at least in part on medical-related information previously collected for other patients. The knowledge artifact may be included in a list of knowledge artifacts that may include internal knowledge artifacts, external knowledge artifacts, and a combination of internal and external knowledge artifacts. An knowledge artifact is an organization of medical-related information in a manner that is readable by a medical suggestion engine to implement techniques described herein.

At 1308, the process 1300 generates medical suggestions based at least in part on the medical context and the knowledge artifact. The medical suggestions may correspond to one or more possible courses of treatment for the care scenario of the patient. For example, the medical suggestions may include suggestions that, based on the medical context for a patient and a knowledge artifact collected for similar patients, the patient should be removed from a drug, be administered a test, or some other similar course of treatment. The medical suggestions may indicate a mapping of courses of treatment to outcomes based on the courses of treatment. The more successful courses of treatment may have a greater weighting. The medical suggestions may also be provided in a list of medical suggestions that may rank medical suggestions based on criticality. In some examples, the medical suggestions may be generated in a manner that provide the best possible outcomes in the most cost efficient manner. For example, when the medical suggestion relates to diagnostic testing, the medical suggestions may be generated based on the cost of available and applicable diagnostic testing.

At 1310, the process 1300 provides a portion of the medical suggestions to a user device. This may include providing one or more medical suggestions for presentation on a user interface of a user device. The user device may be associated with the medical care professional. Thus, the medical care professional that is treating the patient may receive one or more medical suggestions pertaining to the treatment of the patient. The medical suggestions may be tailored to the particular medical care professional by considering his or her specialty, preferences, patterns of treatment and the like, and be tailored to the patient by considering his or her medical history and current care scenario.

Figure 14:
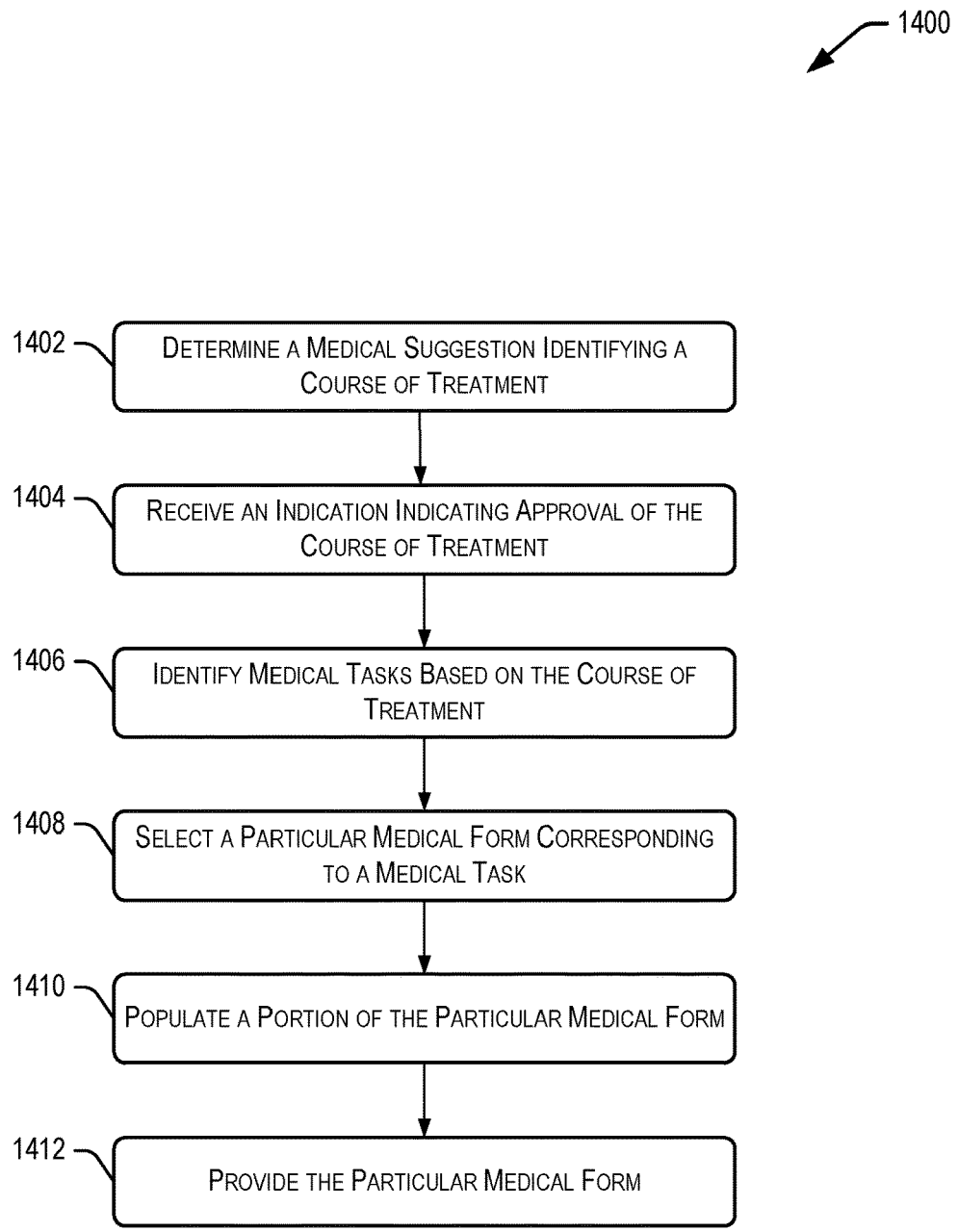
FIG. 14 is a flow diagram depicting example acts for implementing techniques relating to generating contextual suggestions and providing contextual suggestions to authorized users as described herein, according to at least one example.

FIG. 14 illustrates a flowchart of a process 1400 for populating a medical form based on a medical suggestion according to an embodiment of the invention. The process 1400 begins at block 1402 by determining a medical suggestion identifying a course of treatment. The medical suggestion may be determined based at least in part on a knowledge artifact as described herein. The course of treatment may be particular to a patient and/or may be general for any patient sharing similar characteristics as identified by the knowledge artifact. The medical suggestion may also depend on a medical context for the treatment of the patient.

At 1404, the process 1400 receives an indication indicating approval of the course of treatment. The indication may be received from the medical care professional. The indication may indicate approval of the course of treatment identified by the medical suggestion. This may involve the medical care professional selecting a course of treatment via a user interface after the suggestion has been made to the medical care professional and presented at the user interface. In some examples, the medical care professional adjusts the course of treatment prior to indicating his or her approval. Thus, in some examples, the approved course of treatment may be a revised and/or adjusted course of treatment. In some examples, the medical care professional inputs his or her own course of treatment.

At 1406, the process 1400 identifies medical tasks based on the course of treatment. At least some of the medical tasks may involve submission of a medical form as a precondition to performance of the medical task. For example, prior to fulfilling a prescription for a drug (e.g., a medical task) to treat a cold (e.g., a course of treatment), a prescription (e.g., a form) must be filled out and signed by the medical care professional (e.g., a precondition). Other forms for other medical tasks may also be required prior to performance of the other medical tasks.

At 1408, the process 1400 selects a particular medical form corresponding to the medical task. The selecting may be based on a user input indicating the particular medical form and/or may be performed programmatically depending on the course of treatment for the patient, preferences of the medical care professional, and the like. The particular medical form may be selected from a list of medical forms pertaining to the same medical task. For example, for a referral to orthopedic surgeon A, referral from A may be required, for a referral to orthopedic surgeon B, a referral from B may be required, and so forth. The particular medical form may be selected from a list of medical forms pertaining to different medical tasks. For example, for a referral to orthopedic surgeon A, referral form A may be required, for a lab test B, a lab test request form B may be required, and so forth.

At 1410, the process 1400 populates a portion of the particular medical form. This may include populating the medical form with patient information from a patient record of the patient or profile information of the medical care professional. Populating the portion of the particular medical form may also include populating a portion of the fields of the particular medical form.

At 1412, the process 1400 provides the particular medical form. Providing the particular medical form may involve providing the form to a different medical care professional for performance of the medical task associated with the medical task.

Figure 15:
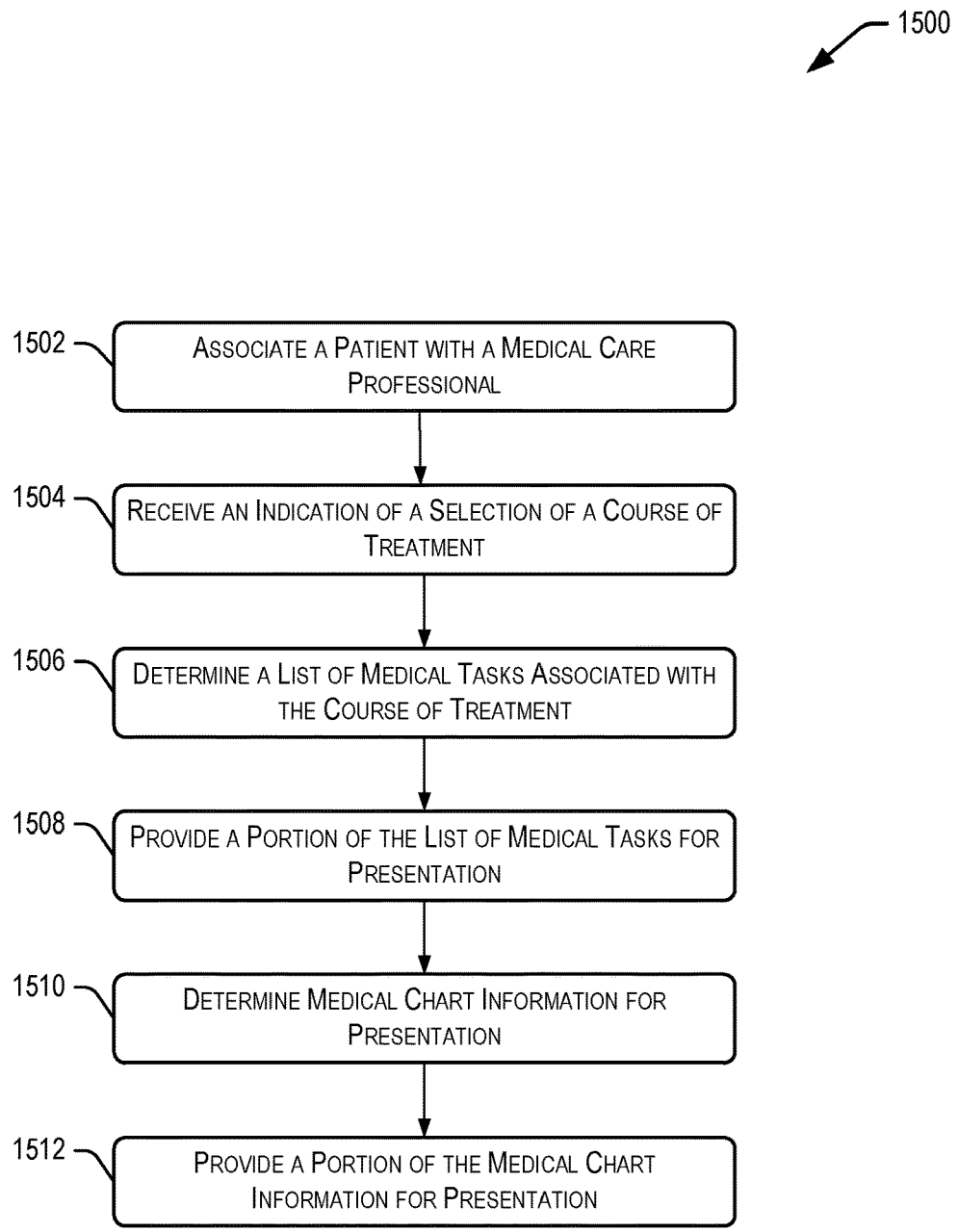
FIG. 15 is a flow diagram depicting example acts for implementing techniques relating to generating contextual suggestions and providing contextual suggestions to authorized users as described herein, according to at least one example.

FIG. 15 illustrates a flowchart of a process 1500 for providing medical tasks associated with a patient for presentation according to an embodiment of the invention. The process 1500 begins at block 1502 by associating a patient with a medical care professional. The medical care professional may belong to a medical provider network. Associating the patient with the medical care professional may involve identifying in a database of the medical care provider network that the patient has implicitly or explicitly requested treatment from the medical care professional.

At 1504, the process 1500 receives an indication of a selection of a course of treatment. The medical care professional may select the course of treatment by selecting the course of treatment from a list of possible courses of treatment based on the care scenario. In some examples, the course of treatment may be determined by evaluating a patient medical record and/or a profile for the medical care professional.

At 1506, the process 1500 determines a list of medical tasks associated with the course of treatment. The list of medical tasks may comprise a list of medical suggestions. The list of medical tasks may be determined based at least in part on profile information for the medical care professional and a portion of the patient record of the patient.

At 1508, the process 1500 provides a portion of the list of medical tasks for presentation. In some examples, the portion of the list of medical tasks is provided for presentation in a primary area of a user interface of a user device associated with the medical care professional. The portion of the list of medical tasks may include one or more medical tasks. The one or more medical tasks may be weighted, prioritized, and/or ranked in a manner that accounts for medical criticality of the medical task, acceptance of the task by others, preferences of the medical care professional, and other factors. The one or more medical tasks may be presented based on state of the patient (e.g., the patient is a stroke patient, so present medical task A now) or based on time (e.g., the patient just became a patient of the medical care professional, so present medical task B now). At 1508, the process 1500 also determines how to present the one or more medical tasks in a manner that emphasizes the criticality of certain medical tasks over others. More critical medical tasks may be presented in a more invasive manner (e.g., centered on the user interface, including large font, bright colors, flashing, as a pop-up, require a click-through to close, and other similar techniques). Less critical tasks may be presented in a less invasive manner. Such less critical tasks may include considerations that the medical care professional should take in to account as a best practice (e.g., "When a patient is diagnosed with heart disease, other doctors request lab X be performed periodically, have you considered ordering lab X for the patient?"). For example, the rules to generate and present the less critical tasks may indicate prior practices of the medical care professional (e.g., "You typically prescribe drug X, would you like to prescribe drug X to this patient?").

In some examples, the one or more medical tasks may be overridden by the medical care professional. The number of overrides may be recorded for each recommended medical task. When an override rate exceeds a particular threshold, it may be flagged and provided to an authorized user for review. An excessive amount of overrides may indicate that the suggested medical task is not appropriate, is irrelevant, or that medical care professionals do not have a preference for the medical task. In some examples, the success rates for accepted medical tasks may be tracked and may be compared to the clinical result for the particular patient for which the medical task was performed. In this manner, the medical outcome for each suggested medical task can be tracked. In some examples, if the medical care professional accepts a suggested medical task from a first list, the techniques described herein may generate a second list of medical tasks. Thus, the selection of the suggested medical task may prompt the generation and presentation of other medical tasks. In some examples, this process may continue until there are no medical tasks to suggest. In some examples, which medical tasks are suggested depends on the geographic location where the patient is located. For example, in a first geographic area experiencing an outbreak of the flu, a first medical task may be suggested for the patient. However, for the same patient in a second geographic area (not experiencing an outbreak of the flu), a second medical task may be suggested for the patient. In this manner, the techniques described herein provide suggested medical tasks based on the context in which the medical care professional is practicing. This context is what makes the suggestions and other information meaningful.

At 1510, the process 1500 determines medical chart information for presentation. In some examples, the medical chart information is determined based on one or more settings and/or preferences provided by the medical care professional. The medical chart information may include general chart information that is relevant to all medical decisions and specialty chart information that may be organized according to specialty (e.g., orthopedics, oncology, neurology, etc.). A medical care professional may subscribe to receive specialty chart information and the general chart information as a data feed. In some examples, certain medical care professionals may be interested in viewing information for specialties outside of their general area of practice. This preference is accounted for in determining medical chart information.

At 1512, the process 1500 provides a portion of the medical chart information for presentation. This may include presenting medical chart information based on one or more settings and/or preferences provided by the medical care professional. The portion of the medical chart information is presented in a secondary area of the user interface in a manner that emphasizes the list of medical tasks presented in the primary area. The secondary area may be secondary because of where it is placed relative other areas and/or because of how the second area is laid out.

Figure 16:
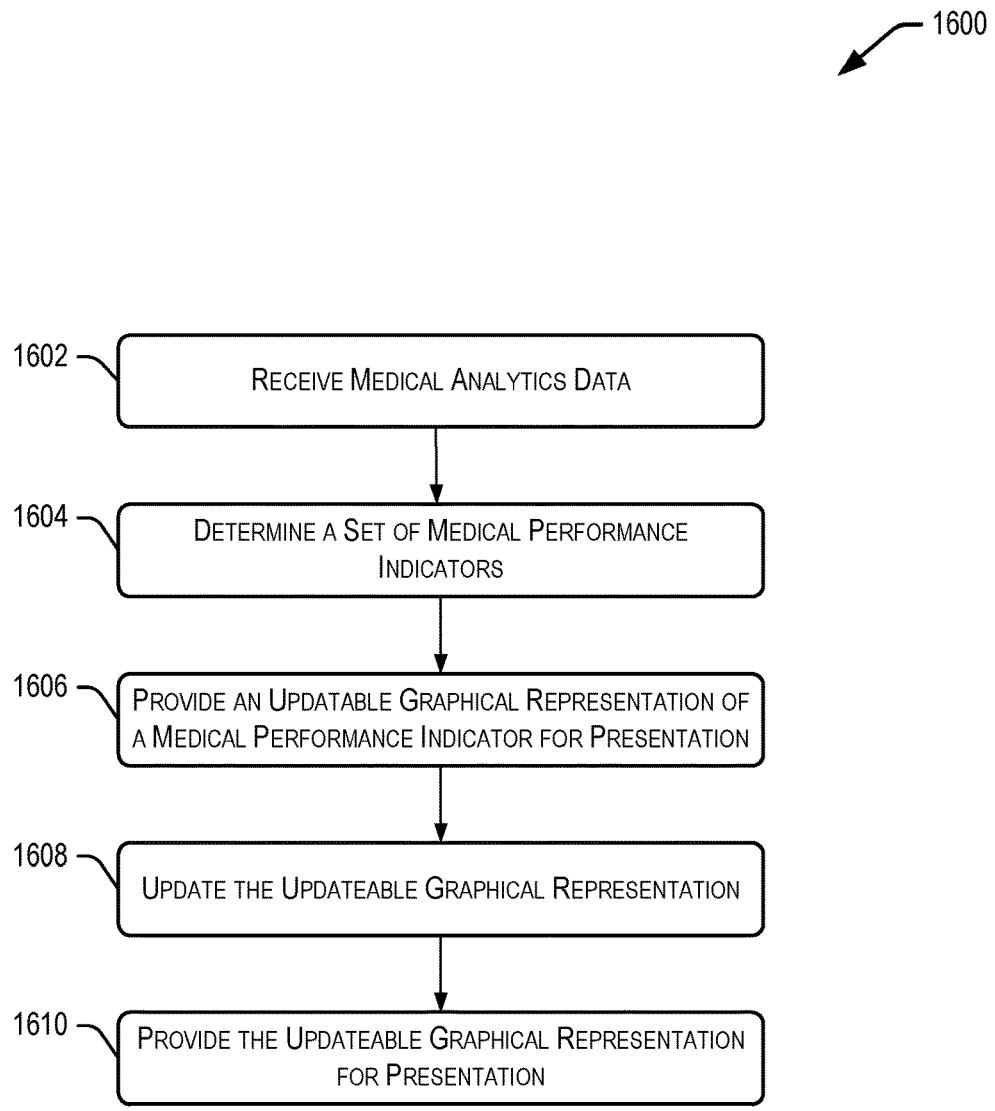
FIG. 16 is a flow diagram depicting example acts for implementing techniques relating to generating contextual suggestions and providing contextual suggestions to authorized users as described herein, according to at least one example.

FIG. 16 illustrates a flowchart of a process 1600 for providing medical performance indicators for presentation according to an embodiment of the invention. The process 1600 begins at block 1602 by receiving medical analytics data. In some examples, the medical analytics data is collected from at least one medical care facility including a plurality of medical care professionals. In some examples, the medical analytics data is collected from a plurality of medical care facilities extending throughout many geographic areas. In some examples, the medical analytics data is organized prior to being received at 1602.

At 1604, the process 1600 determines a set of medical performance indicators. In some examples, the set of medical performance indicators correspond to a medical care professional. The medical performance indicators may also be determined based at least in part on the medical analytics data. The medical performance indicators may include indicators that can be used to rate, evaluate, judge, or otherwise compare the medical care professional to a baseline or to other medical care professionals.

At 1606, the process 1600 provides an updateable graphical representation of the a medical performance indicator for presentation. The updateable graphical representation may be presented on a user interface of a user device associated with the medical care professional. The updatable graphical representation may be representative of a particular medical performance indicator. The updateable graphical representation may be updated periodically, in accordance with a rule, or in any other suitable manner to ensure that the updatable graphical representation represents current medical analytics data. Examples of the updatable graphical representation include bar graphs, tables, lists, pie charts, line graphs, Venn diagrams, and other methods of presenting medical analytics data.

At 1608, the process 1600 updates the updateable graphical representation. This may involve updating the updatable graphical representations in response to a change of a portion of the medical analytics data corresponding to the performance indicator. In some examples, the updatable graphical representation is updated in accordance with one or more rules, which may be user-defined and/or machine-defined.

At 1610, the process 1600 provides the updated graphical representation for presentation. In some examples, this may involve providing the updated graphical representation for presentation on the user interface of the user device.

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to, portable or fixed storage devices, optical storage devices, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A system for presenting tasks, the system comprising:
   a memory configured to store computer-executable instructions;
   an input component;
   a display configured to present a contextual user interface; and
   a processor in communication with the memory and configured to execute the computer-executable instructions to perform operations comprising:
      receiving, via the input component, an indication of a selection of an action course for a dependent user, the dependent user associated with an authorized user who is authorized to attend to the dependent user to conduct the action course for the dependent user;
      receiving a set of tasks associated with the action course, the set of tasks generated based on (i) the action course that corresponds to a medical treatment, (ii) profile data corresponding to a profile of the authorized user that corresponds to a care provider, and (iii) record data corresponding to a record of the dependent user that corresponds to a patient, the set of tasks comprising at least one of:
         a first task that can be performed by the authorized user and which corresponds to conducting the action course for the dependent user; or
         a second task that can be authorized by the authorized user, performed by a different authorized user, and which corresponds to conducting the action course for the dependent user;
      for each task of the set of tasks associated with the action course, identifying a criticality level from a plurality of critical levels as corresponding to the task;
      presenting the set of tasks within the contextual user interface in accordance with a set of presentation rules where, for each task, a manner of presenting of the task is selected from a plurality of presentation options based on the criticality level identified as corresponding to the task, where the manner of presenting of the task corresponds to graphically differentiating the task from other tasks of the set of tasks;
      selecting certain record data corresponding to the record of the dependent user in accordance with the set of presentation rules; and
      presenting, within the contextual user interface, the certain record data corresponding to the record of the dependent user in accordance with the set of presentation rules;
      wherein presentation of the first task or the second task in a first area of the contextual user interface is emphasized when compared to presentation of the certain record data in a second area of the contextual user interface, and
      wherein selection of a user interface component corresponding to one of the tasks begins a workflow that automatically identifies and populates a form corresponding to the one of the tasks.

2. The system of claim 1, wherein the first task comprises at least one of a referral task, an education task, or a review task.

3. The system of claim 2, wherein:
   selection of a first user interface component corresponding to the referral task begins a referral workflow usable by the authorized user to refer the dependent user to another authorized user;
   selection of a second user interface component corresponding to the education task enables the authorized user to conduct one or more education modules corresponding to the action course; and selection of a third user interface component corresponding to the review task enables the authorized user to review suggestions for conducting the action course for the dependent user.

4. The system of claim 1, wherein:

the second task is an order task; and selection of a user interface component corresponding to the order task begins an order workflow usable by the authorized user to submit an order for the dependent user.

5. The system of claim 1, wherein the second area comprises a plurality of subareas and the certain record data comprises specialized record data selected to be relevant to a specialized authorized user and generic record data selected to be relevant to the authorized user and the specialized authorized user.

6. The system of claim 5, wherein:

presenting, within the second area of the contextual user interface, the certain record data comprises:

presenting the specialized record data in a first subarea of the plurality of subareas; and presenting the generic record data in a second subarea of the plurality of subareas; and presentation of the generic record data in the second subarea is emphasized when compared to presentation of the specialized record data in the first subarea.

7. The system of claim 1, where the identifying the criticality level from the plurality of critical levels as corresponding to the task comprises:

determining the criticality level of the first task or the criticality level of the second task as being greater than one or more other criticality levels of one or more other tasks.

8. The system of claim 7, where the manner of presenting the first task or the second task corresponds to centering an interface element corresponding to the first task or the second task with respect to the contextual user interface and requiring a click-through to close the interface element corresponding to the first task or the second task.

9. A computer-implemented method for presenting tasks, the method comprising:

receiving an indication of a selection of an action course for a dependent user, the dependent user associated with an authorized user who is authorized to attend to the dependent user to conduct the action course for the dependent user;

generating a set of tasks associated with the action course based on (i) the action course that corresponds to a medical treatment, (ii) profile data corresponding to a profile of the authorized user that corresponds to a care provider, and (iii) record data corresponding to a record of the dependent user that corresponds to a patient, the set of tasks comprising at least one of:

a first task that can be performed by the authorized user and which corresponds to conducting the action course for the dependent user; or a second task that can be authorized by the authorized user, performed by a different authorized user, and which corresponds to conducting the action course for the dependent user;

for each task of the set of tasks associated with the action course, identifying a criticality level from a plurality of critical levels as corresponding to the task;

presenting the set of tasks within a contextual user interface in accordance with a set of presentation rules where, for each task, a manner of presenting of the task is selected from a plurality of presentation options based on the criticality level identified as corresponding to the task, where the manner of presenting of the task corresponds to graphically differentiating the task from other tasks of the set of tasks;

determining certain record data corresponding to the record of the dependent user in accordance with the set of presentation rules; and providing, for presentation within the contextual user interface, the certain record data corresponding to the record of the dependent user in accordance with the set of presentation rules;

wherein selection of a user interface component corresponding to one of the tasks begins a workflow that automatically identifies and populates a form corresponding to the one of the tasks.

10. The computer-implemented method of claim 9, wherein the first task comprises at least one of a referral task, an education task, or a review task.

11. The computer-implemented method of claim 10, wherein:

selection of a first user interface component corresponding to the referral task begins a referral workflow usable by the authorized user to refer the dependent user to another authorized user;

selection of a second user interface component corresponding to the education task enables the authorized user to conduct one or more education modules corresponding to the action course; and selection of a third user interface component corresponding to the review task enables the authorized user to review suggestions for conducting the action course for the dependent user.

12. The computer-implemented method of claim 9, wherein:

the second task is an order task; and selection of a user interface component corresponding to the order task begins an order workflow usable by the authorized user to submit an order for the dependent user.

13. The computer-implemented method of claim 9, wherein presentation of the first task or the second task in a first area is emphasized when compared to presentation of the certain record data in a second area.

14. The computer-implemented method of claim 13, wherein:

providing, for presentation within the second area of the contextual user interface, the certain record data comprises:

providing specialized record data for presentation within a first subarea of a plurality of areas; and providing generic record data for presentation in a second subarea of a plurality of subareas; and presentation of the generic record data in the second subarea is emphasized when compared to presentation of the specialized record data in the first subarea.

15. The computer-implemented method of claim 13, wherein the second area comprises a plurality of subareas and the certain record data comprises specialized record data selected to be relevant to a specialized authorized user and generic record data selected to be relevant to the authorized user.

16. One or more computer-readable storage devices that are non-transitory and that store computer-executable instructions which, when executed by one or more computer systems, configure the one or more computer systems to perform operations for presenting tasks, the operations comprising:
    receiving an indication of a selection of an action course for a dependent user, the dependent user associated with an authorized user who is authorized to attend to the dependent user to conduct the action course for the dependent user;
    generating a set of tasks associated with the action course based on (i) the action course that corresponds to a medical treatment, (ii) profile data corresponding to a profile of the authorized user that corresponds to a care provider, and (iii) record data corresponding to a record of the dependent user that corresponds to a patient, the set of tasks comprising at least one of:
        a first task that can be performed by the authorized user and which corresponds to conducting the action course for the dependent user; or
        a second task that can be authorized by the authorized user, performed by a different authorized user, and which corresponds to conducting the action course for the dependent user;
    for each task of the set of tasks associated with the action course, identifying a criticality level from a plurality of critical levels as corresponding to the task;
    presenting the set of tasks within a contextual user interface in accordance with a set of presentation rules where, for each task, a manner of presenting of the task is selected from a plurality of presentation options based on the criticality level identified as corresponding to the task, where the manner of presenting of the task corresponds to graphically differentiating the task from other tasks of the set of tasks;
    determining certain record data corresponding to the record of the dependent user in accordance with the set of presentation rules; and
    providing, for presentation within the contextual user interface, the certain record data corresponding to the record of the dependent user in accordance with the set of presentation rules;
    wherein selection of a user interface component corresponding to one of the tasks begins a workflow that automatically identifies and populates a form corresponding to the one of the tasks.

17. The one or more computer-readable storage devices of claim 16, wherein the first task comprises at least one of a referral task, an education task, or a review task.

18. The one or more computer-readable storage devices of claim 17, wherein:
    selection of a first user interface component corresponding to the referral task begins a referral workflow usable by the authorized user to refer the dependent user to another authorized user;
    selection of a second user interface component corresponding to the education task enables the authorized user to conduct one or more education modules corresponding to the action course; and
    selection of a third user interface component corresponding to the review task enables the authorized user to review suggestions for conducting the action course for the dependent user.

19. The one or more computer-readable storage devices of claim 16, wherein:
    the second task is an order task; and
    selection of a user interface component corresponding to the order task begins an order workflow usable by the authorized user to submit an order for the dependent user.

20. The one or more computer-readable storage devices of claim 16, wherein presentation of the task in a first area is emphasized when compared to presentation of the certain record data in a second area, and wherein the second area comprises a plurality of subareas and the certain record data comprises specialized record data selected to be relevant to a specialized authorized user and generic record data selected to be relevant to the authorized user and the specialized authorized user.

21. The one or more computer-readable storage devices of claim 20, wherein:
    providing, for presentation within the second area of the contextual user interface, the certain record data comprises:
        providing the specialized record data for presentation in a first subarea of the plurality of subareas; and
        providing the generic record data for presentation in a second subarea of the plurality of subareas; and
    presentation of the generic record data in the second subarea is emphasized when compared to presentation of the specialized record data in the first subarea.

* * * * *